(12) United States Patent
Kawano et al.

(10) Patent No.: US 7,727,974 B2
(45) Date of Patent: Jun. 1, 2010

(54) METHODS OF REDUCING THE SEVERITY OF MUCOSITIS

(75) Inventors: Tetsu Kawano, Hyogo (JP); Seiichi Kobayashi, Ibaraki (JP); Minghuang Zhang, Windham, NH (US); Hiroshi Shirota, Belmont, MA (US)

(73) Assignee: Eisai R & D Management Co., Ltd., Tokyo (JP)

( * ) Notice: Subject to any disclaimer, the term of this patent is extended or adjusted under 35 U.S.C. 154(b) by 235 days.

(21) Appl. No.: 11/434,019

(22) Filed: May 15, 2006

(65) Prior Publication Data

US 2007/0072824 A1 Mar. 29, 2007

Related U.S. Application Data

(63) Continuation-in-part of application No. 10/486,455, filed as application No. PCT/US02/25452 on Aug. 12, 2002, now abandoned.

(60) Provisional application No. 60/680,733, filed on May 13, 2005, provisional application No. 60/311,325, filed on Aug. 10, 2001.

(51) Int. Cl.
*A61K 31/7016* (2006.01)
(52) U.S. Cl. ..................................................... 514/53
(58) Field of Classification Search ........................ None
See application file for complete search history.

(56) References Cited

U.S. PATENT DOCUMENTS

| 5,041,427 | A | * | 8/1991 | Takayama et al. ............. 514/53 |
| 5,681,824 | A | * | 10/1997 | Christ et al. ................... 514/53 |
| 5,935,938 | A | | 8/1999 | Christ et al. |
| 5,952,309 | A | | 9/1999 | Rossignol et al. |
| 6,184,366 | B1 | | 2/2001 | Christ et al. |
| 2003/0130212 | A1 | | 7/2003 | Rossignol et al. |
| 2005/0215517 | A1 | | 9/2005 | Rossignol et al. |

FOREIGN PATENT DOCUMENTS

| WO | WO 00/41703 | 7/2000 |
| WO | WO 01/37843 | 5/2001 |
| WO | WO 01/43691 | 6/2001 |
| WO | WO 01/60382 | 8/2001 |
| WO | WO 01/93921 | 12/2001 |
| WO | WO 03/013440 | 2/2003 |
| WO | WO 03/105861 | 12/2003 |

OTHER PUBLICATIONS

Sonis, S. "Mucositis as a biological process . . ." Oral Oncology (1998) vol. 34, pp. 39-43.*
Feld, R. "The role of surveillance cultures . . ." Support Care Cancer (1997) vol. 5, pp. 371-375.*
Vosika, G. et al "Phase I study of intravenous modified Lipid A" Cancer Immunol. Immunother. (1984) vol. 18, pp. 107-112.*
Kwong, K. "Prevention and treatment of oropharyngeal mucositis . . ." Cancer Nursing (2004) vol. 27, No. 3, pp. 183-205.*
Kostler, W. et al "Oral mucositis complicating chemotherapy . . ." Cancer J. Clin. (2001) vol. 51, pp. 290-315.*
Asea et al., "Novel Signal Transduction Pathway Utilized by Extracellular HSP70," J. Biol. Chem. 277:15028-15034, 2002.
Chow et al., "Toll-Like Receptor-4 Mediates Lipopolysaccharide-Induced Signal Transduction," J. Biol. Chem. 274: 10689-10692, 1999.
Christ et al., "E5531, A Pure Endotoxin Antagonist of High Potency," Science 268:80-83, 1995.
Fort et al., "A Synthetic TLR4 Antagonist Has Anti-Inflammatory Effects in Two Murine Models of Inflammatory Bowel Disease," J. Immunol. 174:6416-6423, 2005.
Hill et al., "The Primacy of the Gastrointestinal Tract as a Target Organ," Blood 95:2754-2759, 2000.
Ingalls et al., "Membrane-Associated Proteins of a Lipopolysaccharide-Deficient Mutant of *Neisseria meningitidis* Activate the Inflammatory Reponse Through Toll-Like Receptor 2," Infect. Immun. 69:2230-2236, 2001.
Lien et al., "A Novel Synthetic Acyclic Lipid A-Like Agonist Activates Cells via the Lipopolysaccharide/Toll Like Receptor 4 Signaling Pathway," J. Biol. Chem. 276:1873-1880, 2001.
Means et al., "The Biology of Toll-Like Receptors," Cytokine Growth Factor Rev. 11:219-232, 2000.
Means et al., "Differential Effects of a Toll-Like Receptor Antagonist on Mycobacterium Tuberculosis-Induced Macrophage Responses," J. Immunol. 166:4074-4082, 2001.
Ohashi et al., "Cutting Edge: Heat Shock Protein 60 is a Putative Endogenous Ligand of the Toll-Like Receptor-4 Complex," J. Immunol. 164:558-561, 2000.
Sasu et al., "*Chlamydia pneumoniae* and Chlamydial Heat Shock Protein 60 Stimulate Proliferation of Human Vascular Smooth Muscle Cells Via Toll-Like Receptor 4 and p44/p42 Mitogen-Activated Protein Kinase Activation," Circ. Res. 89:244-250, 2001.
Sonis, "A Biological Approach to Mucositis," J. Support Oncol. 2:21-36, 2004.
Takeuchi et al., "Differential Roles of TLR2 and TLR4 in Recognition of Gram-Negative and Gram-Positive Bacterial Cell Wall Components," Immunity 11:443-451, 1999.
Zhang et al., "LPS Antagonist E5564 Antagonizes Heat Shock Protein (HSP) 60 and 70 Elicited Innate Immune Activation," J. Endotoxin Res. 8:201 (Abstract), 2002.
European Search Report, Jun. 25, 2007 (EP Application No. 02757067.0; Search Completed Jun. 15, 2007).
International Search Report from International Application No. PCT/IB2006/003538 dated Jun. 27, 2007.

* cited by examiner

*Primary Examiner*—Leigh C Maier
(74) *Attorney, Agent, or Firm*—McCarter & English, LLP

(57) ABSTRACT

The invention provides methods of reducing the severity of mucositis, involving administration of a toll-like receptor 4 antagonist.

19 Claims, 20 Drawing Sheets

METHODS OF REDUCING THE SEVERITY OF MUCOSITIS

CROSS-REFERENCE TO RELATED APPLICATIONS

This application is a continuation-in-part of U.S. Ser. No. 10/486,455, filed Jul. 26, 2004, which is a filing under 35 U.S.C. §371 of PCT/US02/25452, filed Aug. 12, 2002, which claims priority under 35 U.S.C. §119(e) from U.S. Ser. No. 60/311,325, filed Aug. 10, 2001. This application also claims priority under 35 U.S.C. §119(e) from U.S. Ser. No. 60/680,733, filed May 13, 2005. The contents of each of the prior applications are incorporated herein by reference.

BACKGROUND OF THE INVENTION

This invention relates to methods for reducing the severity of mucositis.

Mucositis is a condition characterized by swelling, irritation, and discomfort of mucosal linings such as those of the gastrointestinal tract and the oral and oralpharyngeal cavities, and can result in mouth and throat sores, diarrhea, abdominal cramping and tenderness, and rectal ulcerations. This condition occurs in approximately half of all cancer patients, and is a common side effect of cancer treatments involving radiation and/or chemotherapy. The goal of these approaches to cancer treatment is to kill rapidly dividing cancer cells but, unfortunately, other rapidly dividing cells are killed by the treatment as well, including cells that line regions such as the gastrointestinal tract, leading to mucositis. Symptoms of mucositis generally occur five to ten days after the start of cancer treatment, and can take two to four weeks after cessation of treatment to clear. The incidence of mucositis, as well as its severity, depends on factors such as the type and duration of the cancer treatment. Mucositis occurs, for example, in virtually all patients who are treated by irradiation of the head and neck. It is also highly prevalent in patients treated with high dose chemotherapy and/or irradiation for the purpose of myeloablation, in preparation for stem cell or bone marrow transplantation.

Mucositis adversely impacts the quality of life of cancer patients in several ways. For example, the mouth and throat sores of mucositis can cause significant pain and make it difficult to eat, drink, and even take oral medication. Mucositis is also accompanied by a severe risk of infection, as it can lead to a breach in the otherwise protective linings of the oral mucosa and gastrointestinal tract, which are colonized by a vast array of microorganisms. Further, efforts to counter the discomforts of mucositis can lead to disruptions in cancer treatment, alterations in treatment dosages, or shifting to different modes of treatment. Severe mucositis can also lead to the need for parenteral nutrition or hospitalization. The development of effective approaches to preventing and treating mucositis is therefore important for improving the care of cancer patients.

SUMMARY OF THE INVENTION

The invention provides methods of reducing the severity of mucositis (e.g., oral or gastrointestinal mucositis) in patients. The methods include a step of administering to the patients a composition containing one or more compounds that block activation of toll-like receptor 4 (TLR4), such as a lipid A analog, which may be within the formula:

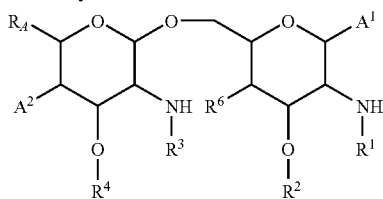

where $R^1$ is selected from the group consisting of:

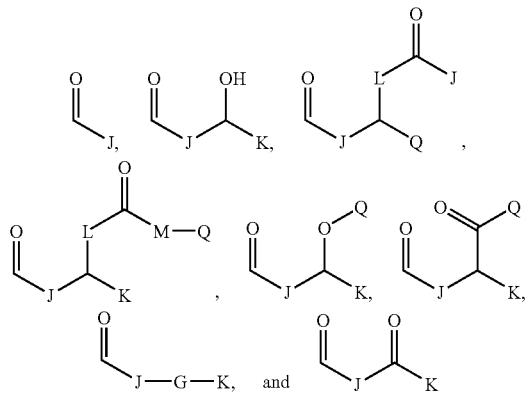

where each J, K, and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of straight or branched C5 to C18 alkyl,

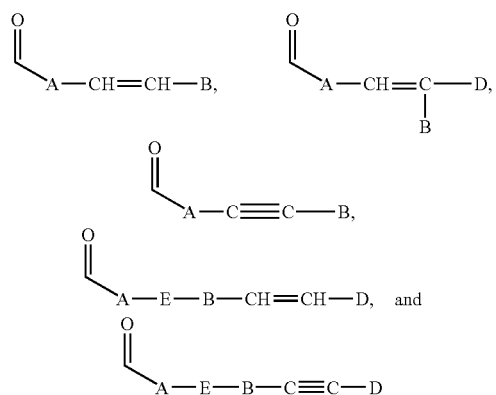

where E is NH, O, S, SO, or $SO_2$; each A, B, and D, independently, is straight or branched C1 to C15 alkyl;

$R^4$ is selected from the group consisting of straight or branched C4 to C20 alkyl, and

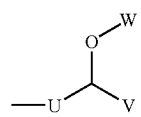

where each U and V, independently, is straight or branched C2 to C15 alkyl and W is hydrogen or straight or branched C1 to C5 alkyl;

$R_A$ is $R^5$ or $R^5$—O—$CH_2$—, $R^5$ being selected from the group consisting of hydrogen, J', -J'-OH, -J'-O—K', -J'-O—K'—OH, and -J'-O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of

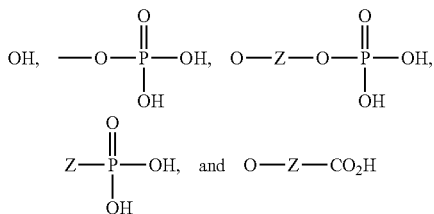

where Z is straight or branched C1 to C10 alkyl; or a pharmaceutically acceptable salt or phosphate ester thereof. One aspect of the invention includes phosphate esters of the above-noted formula, wherein at least one of the hydroxyl groups of $A^1$ or $A^2$ can be substituted to form a phosphate ester.

An example of a Lipid A analog that can be included in the compositions of the invention is a compound having the following structure:

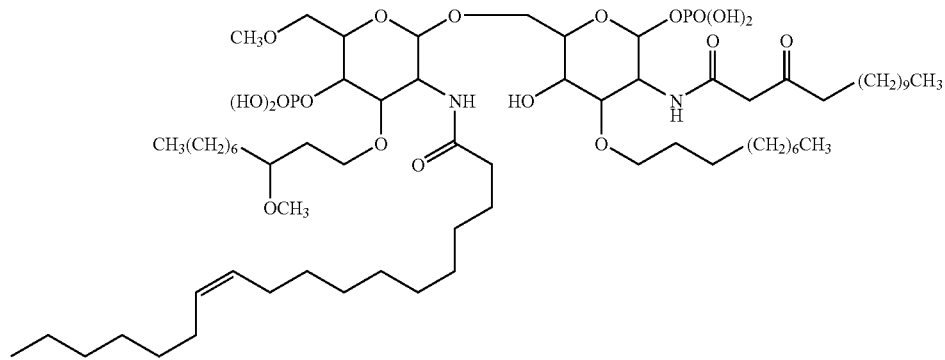

or a pharmaceutically acceptable salt or phosphate ester thereof.

In a more specific example, the compound is of the following structure:

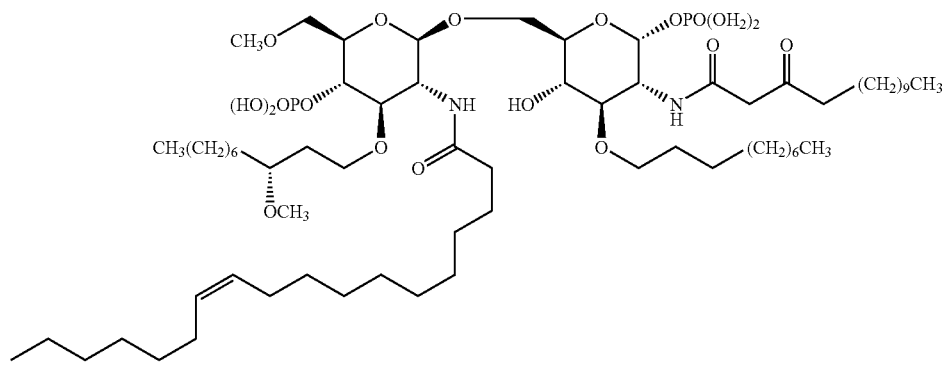

or a pharmaceutically acceptable salt or phosphate ester thereof.

Patients that can be treated according to the invention include those who have mucositis (e.g., oral or gastrointestinal mucositis). In addition, patients who do not have, but are at risk of developing, mucositis (e.g., oral or gastrointestinal mucositis) can be treated according to the invention. In the latter group of patients, the treatment can inhibit or prevent the development of mucositis.

Examples of treatments that may cause or place a patient at risk of developing mucositis (e.g., oral or gastrointestinal mucositis) are radiation therapy and chemotherapy, as described further elsewhere herein or in the background section. Patients that can be treated according to the invention thus include, for example, cancer patients, as well as patients that have recently been, will shortly be, or are currently subject to treatment with head or neck irradiation, or stem cell or bone marrow transplantation.

According to the methods of the invention, compositions used in the invention can be administered to a patient prior to, concurrently with, or after a treatment that has induced or places the patient at risk of developing mucositis (e.g., oral or gastrointestinal mucositis), or a combination of these approaches can be used. In an example, the composition is administered at the same time as, within 1-4 hours of, or on the same day as the treatment, and then for 1-3 (e.g., 1-2) days thereafter (e.g., 1-2 times per day). Other examples of treatment regimens are provided below.

The compositions can be administered to patients by any acceptable manner known in the art, including topically (e.g., by gel, rinse, lozenge, cream, ointment, or patch), by intravenous infusion, orally (e.g., by tablet, capsule, lozenge, cream, ointment, or patch), rectally (e.g., by suppository, ointment, or enema), or vaginally (e.g., by cream, ointment, gel, or suppository). Also, treatment according to the invention can be carried out in combination with other approaches to treating mucositis, including antimicrobial and palliative treatments, as is discussed further below.

Further, the invention includes compositions including the compounds described herein, formulated for administration for reducing the severity of mucositis as described herein. As is described in detail below, these compositions can include the compounds in formulations such as gels for topical administration, rinses, tablets, capsules, chewing gum, lozenges, creams, ointments, enemas, suppositories, or patches.

The invention provides several advantages. For example, in providing approaches to reducing the severity of mucositis, an uncomfortable side effect of treatments such as radiation and chemotherapy, the methods of the invention can contribute to the well being of patients as they face the challenges of such treatments. Further, the methods of the invention can decrease the incidence of infection, which is a common consequence of mucositis. In addition, in providing increased comfort to patients, the methods of the invention can lead to increased compliance of patients with their therapeutic regimens, and also can contribute to increasing the speed of their recovery.

Other features and advantages of the invention will be apparent from the following detailed description, the drawings, and the claims.

DETAILED DESCRIPTION

Figure 1:
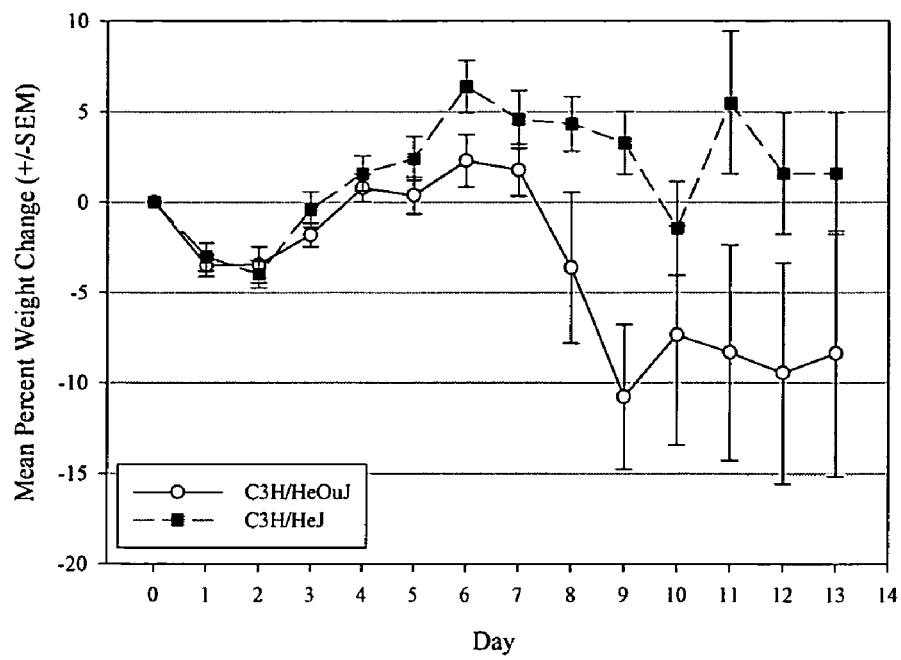
FIG. 1 is a graph showing the percent weight change of C3H/HeOuJ and C3H/HeJ mice after snout irradiation treatment. Animals were weighed daily, the percent weight change from day 0 was calculated, and group means and standard errors of the mean (SEM) calculated for each day.

The present invention provides methods of reducing the severity of mucositis (e.g., oral or gastrointestinal mucositis). The methods can be used to treat patients who already have mucositis. In addition, the methods can also be carried out with patients who do not have, but are at risk of developing mucositis (e.g., cancer or other patients scheduled to receive, currently receiving, or previously treated with radiation and/or chemotherapy). In the latter group of patients, which do not yet have mucositis, treatment according to the invention can reduce the severity of mucositis resulting from their cancer treatment, inhibit the development of mucositis, or prevent mucositis.

The invention is based on the discovery that blocking activation of toll-like receptor 4 (TLR4) provides beneficial therapeutic effects in the reduction of severity of mucositis, as described herein. TLR4 is a receptor for endotoxin, or lipopolysaccharide (LPS), which is shed from the cell walls of growing and dying bacteria and has been associated with the induction of inflammatory responses. According to the present invention, TLR4 receptor activation is blocked by administration of a TLR4 antagonist, leading to beneficial effects in the reduction of severity of mucositis. In addition to blocking endotoxin, treatment according to the invention may block the effects of heat shock proteins (HSP's) in mucositis. In particular, such proteins, which are stress inducible proteins, may be induced during stress including radiation therapy and chemotherapy. HSP60, 70, or 90 may be endogenous ligands of TLR4, and thus may play a role in the mucositis induced by radiation therapy.

TLR4 antagonists used in the methods of the invention can be, for example, analogs of the lipid A region of LPS, such as lipid A analogs that are within the formula set forth above, in the Summary of the Invention. An example of a Lipid A analog that can be included in the compositions of the invention is a compound having the following structure:

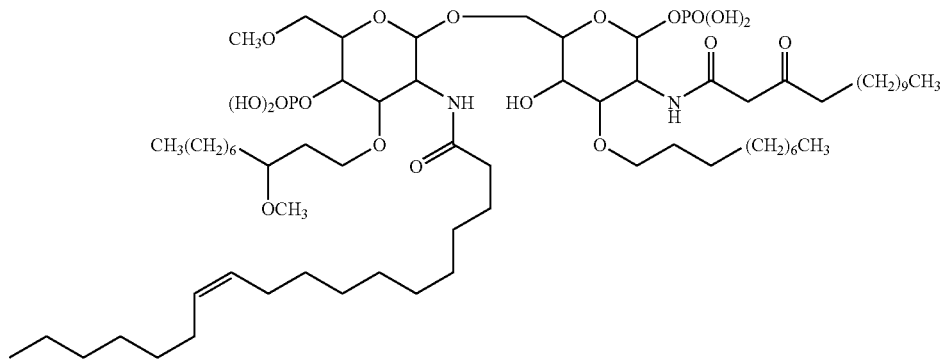

or a pharmaceutically acceptable salt or phosphate ester thereof.

In a more specific example, the compound is of the following structure:

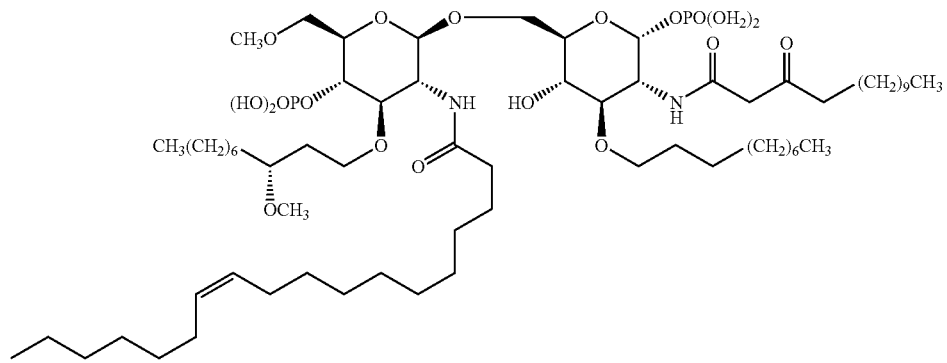

or a pharmaceutically acceptable salt or phosphate ester thereof. This compound, is known as eritoran (also known as compound E5564, compound 1287, and SGEA) and is described in U.S. Pat. No. 5,935,938.

Other examples of compounds that can be used in the invention include the following:

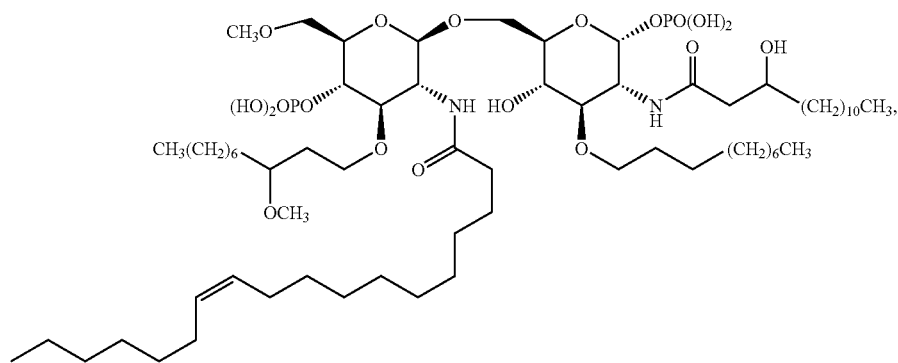

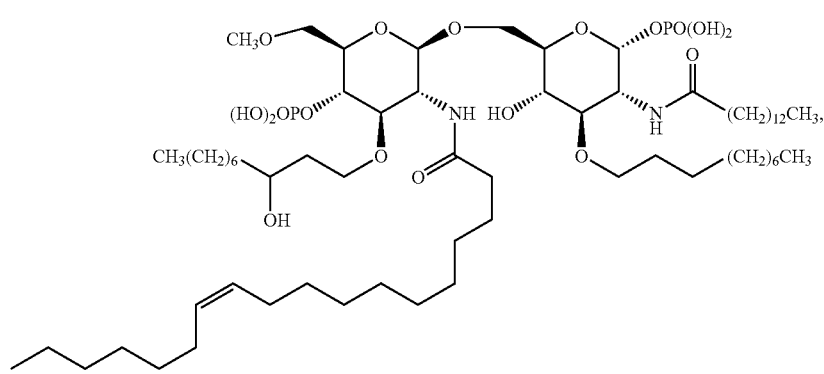

-continued
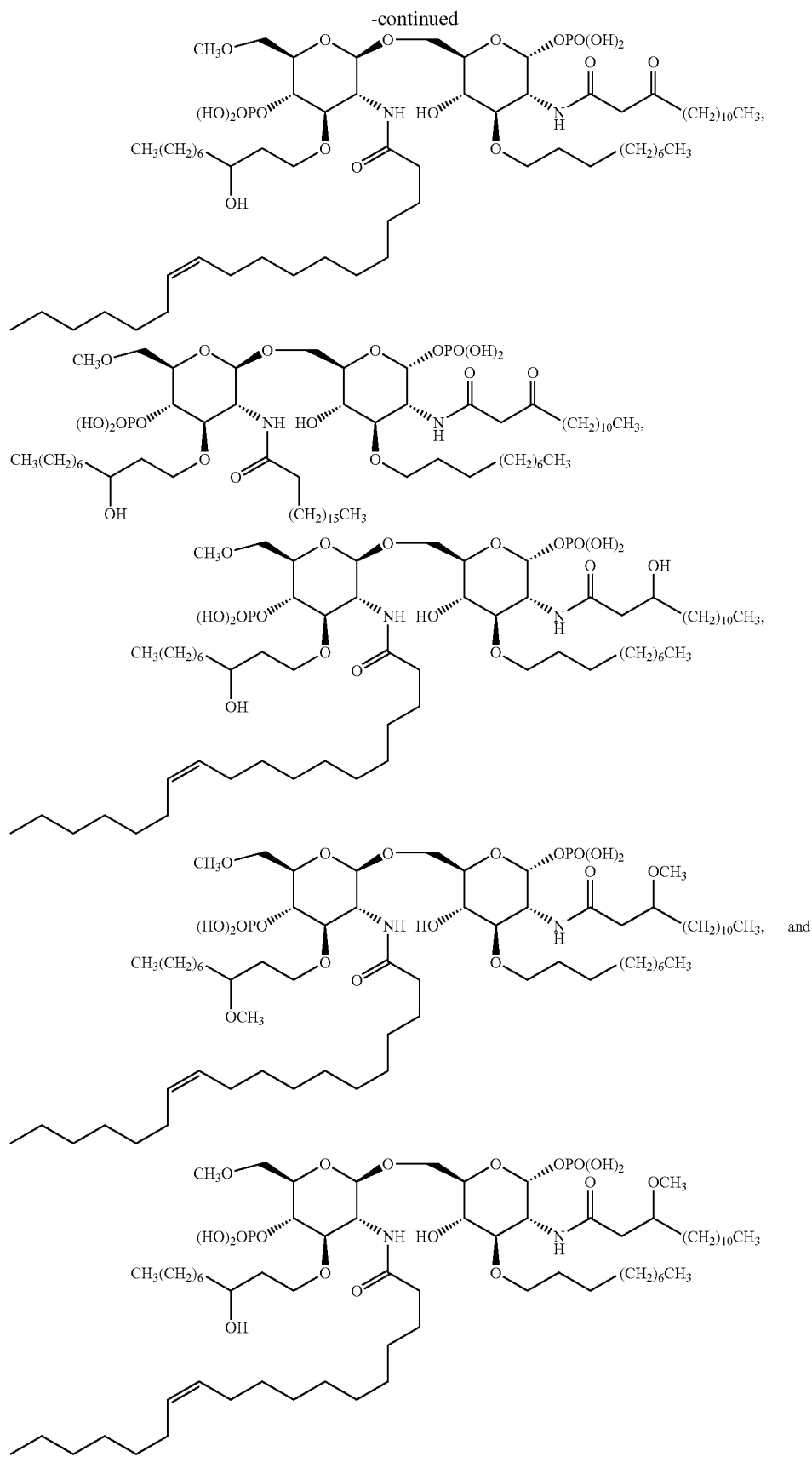

and a pharmaceutically acceptable salt or phosphate ester thereof.

Additional TLR4 antagonists that can be used in the invention include, for example, compound B531 (U.S. Pat. No. 5,530,113), as well as other compounds described in the following patents: U.S. Pat. No. 5,935,938; U.S. Pat. No. 5,612,476; U.S. Pat. No. 5,756,718; U.S. Pat. No. 5,843,918; U.S. Pat. No. 5,750,664; U.S. Pat. No. 6,235,724; U.S. Pat. No. 6,184,366; and U.S. Pat. No. 5,681,824. Methods for making these compounds are also described in these documents. Additional methods for making such drugs are described, for example, in WO 02/94019.

According to the methods of the invention, a TLR4 antagonist is administered to a patient before, during, and/or after treatment with a therapy that causes mucositis (e.g., oral or gastrointestinal mucositis) or puts the patient at risk of developing such mucositis. As is noted above, such treatments include radiation and chemotherapy, which act by blocking the growth of rapidly dividing cells, such as cancer cells and epithelial cells that line the surfaces of the gastrointestinal, respiratory, and genitourinary tracts. Specific examples of treatments that can lead to mucositis include radiation treatment (e.g., head and/or neck, whole body, targeted, and/or hyperfractionated radiation), as well as chemotherapeutic regimens used in the treatment of, or as adjuvant treatments for, conditions such as breast cancer, colon cancer, gastric cancer, genitourinary (e.g., bladder, prostate, or testicular) cancer, gynecologic (e.g., cervical, endometrial, ovarian, or uterine) cancer, head and neck/esophageal cancer, leukemia, lung (small cell or non small-cell) cancer, lymphoma (Hodgkin's or non-Hodgkin's), melanoma, multiple myeloma, pancreatic cancer, and sarcoma.

As is known in the art, cancers such as these can be treated using approaches involving immunotherapy by use of agents such as, for example, rituximab, cetuximab, or bevacizumab, alone or in combination with chemotherapy or radiation therapy. In other examples, chemotherapeutic approaches that may induce mucositis include those utilizing (either as single agents or in combinations) platinum derivatives such as carboplatin, cisplatin, and oxaplatin; mitosis inhibitors such as paclitaxel, docetaxel, vinorelbine, vincristine, and vinblastine; topoisomerase inhibitors such as etoposide, irinotecan, and topotecan; antimetabolites such as gemcitabine, capecitabine, fludarabine, methotrexate, 5-fluorouracil, cladribine, pentostatin, and cytarabine; DNA synthesis inhibitors such as doxorubicin, epirubicin, idarubicin, daunorubicin, bleomycin, mechlorethamine, and mitoxantrone; alkylating agents such as cyclophosphamide, ifosfamide, and melphalan carmustine; hormonal oncologics such as estramustine; and agents having other or unknown mechanisms such as dacarbazine. Use of these and other approaches to treating cancer is well known to those of skill in the art.

TLR4 antagonists such as those noted above can be administered using standard methods including, for example, topical approaches and intravenous infusion. The particular approach and dosage used for a particular patient depends on several factors including, for example, the type of cancer treatment, the location(s) of any discomfort, and the general health of patient. Based on factors such as these, a medical practitioner can select an appropriate approach.

Treatment according to the invention can begin prior to cancer treatment (e.g., 1-2 days or up to 1 week prior to cancer treatment), at or near the same time as cancer treatment (e.g., simultaneously with, within 1-4 hours of, or on the same day as cancer treatment), or shortly after the cessation of cancer treatment (e.g., within 1-4 days of cessation, and/or prior to or upon appearance of symptoms). Treatment can then be maintained, for example, until any symptoms of mucositis have substantially cleared or the risk of developing such symptoms has passed. Thus, treatment started before or at or near the same time as cancer treatment can be maintained, e.g., for 1-3, e.g., 1-2 days. In other examples, treatment is maintained for 1-4 or 2-3 weeks following the cessation of cancer treatment, as determined to be appropriate by one of skill in the art. In specific examples, the treatment according to the present invention is carried out prior to cancer treatment only; prior to and concurrently with cancer treatment only; prior to, concurrently with, and after cessation of cancer treatment; concurrently with cancer treatment only; concurrently with and after cessation of cancer treatment only; after cessation of cancer treatment only; or prior to and after cessation of cancer treatment only. Further, treatment according to the methods of the invention can be altered, stopped, or re-initiated in a patient, depending on the status of any symptoms of mucositis. Treatment can be carried out at intervals determined to be appropriate by those of skill in the art. For example, the administration can be carried out 1, 2, 3, or 4 times/day.

In the case of patients having or at risk of developing mucositis in the oral cavity, a TLR4 antagonist, as described herein, can be administered to the oral cavity in the form of a gel, paste, spray, cream, ointment, or patch that is applied to affected or at risk areas. Such patients can also be treated by the use of an oral rinse, chewing gum, or lozenge including the drug. The drug can be administered to patients affected in rectal or vaginal areas by use of formulations in the form of gels, creams, ointments, suspensions, or suppositories. Further, administration can be by use of an enema. In another example, in the case of patients affected in the nasal cavity, the drug can be administered by topical administration, as described herein, or by inhalation of the drug (see, e.g., U.S. Pat. No. 6,683,063). In other approaches, the drug can be administered by injection (e.g., local injection), or by infusion (intravenous or intra-arterial), as discussed further below.

Formulation of drug compounds for use in the modes of administration noted above (and others) are known in the art and are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999.

All patients, and in particular those affected (or at risk) in internal regions that are not readily accessible for topical administration, can be treated by a systemic approach, such as intravenous infusion. This approach to administration may be particularly convenient in the case of patients who already have a catheter in place for the administration of chemotherapeutic or other drugs. Examples of such approaches, in which the drug administered is eritoran (see above) and the indicated amounts of the drug are based on an assumed average weight of a subject of 70 kg, are as follows. In a first example, the drug can be administered at a low dosage by continuous intravenous infusion. As a specific example, the drug can be administered continuously at a rate of 10-500 (e.g., 50-400 or 100-200) μg/hour over the course of the treatment. In another example, in which a patient requires longer-term care, the drug can be administered intermittently (e.g., every 12-24 hours) at a dosage of, for example, 0.1-20 (e.g., 1-8, 2-7, 3-6, or 4-5) mg/hour for 2-6 (e.g., approximately 4) hours. In a variation of this appr the initial or loading dose is followed by maintenance doses that are less than (e.g., half) the loading dose or by continuous infusion as described above in the first example. The duration of such treatment can be determined by those of skill in the art, based on factors such as, for example, the severity of the condition and the observation of improvements. Additional details concerning the use of infusion to administer TLR4 antagonists, such as eritoran, are provided in US-2003-0105033-A1 (bolus or intermittent infusion) and WO 00/41703 (continuous infusion), the contents of each of which are incorporated herein by reference.

When administering the compound eritoran by intravenous infusion, it is preferable to use devices and equipment (e.g., catheters, such as central or peripheral venous catheters, tubing, drip chambers, flashback bulbs, injection Y sites, stopcocks, and infusion bags) that are compatible with the drug. In particular, catheters including a chlorhexidine-based antimicrobial coating have been found to disrupt the size of the micelles of the drug that are formed during formulation, leading to inadequate concentrations in blood. Thus, it is preferable to use devices and equipment that have, for example, a non-chlorhexidine-based antimicrobial coating, such as an antimicrobial coating that includes one or more other antibiotics, such as rifampin or minicyclin.

The invention also includes kits that include one or more TLR4 antagonists (e.g., a Lipid A analog as described above, e.g., the compound eritoran) and instructions to use the drug in the methods described herein. The kits can also optionally include devices or equipment used in administration (e.g., a catheter lacking a chlorhexidine coating) and/or a solution for administering the drug, such as a 5% dextrose (e.g., glucose) solution.

The methods of the invention can be used alone or in conjunction with other approaches to reducing the severity of mucositis. For example, the methods of the invention can be carried out in combination with antimicrobial or antifungal therapies, e.g., therapies involving administration of antibiotics such as nystatin, amphotericin, acyclovir, valacyclovir, clotimazole, and fluconazole. As a specific example of such treatment, patients with head and neck cancer receiving radiotherapy have colonization of the oropharyngeal region with gram-negative bacteria. Selective decontamination of the oral cavity with anti-microbial agents has the benefit of reducing oral mucositis associated with radiation therapy, but there may be limitations to the beneficial effects of such treatment. Anti-microbial therapy can kill bacteria, but cannot reduce endotoxin, and indeed may actually increase endotoxin. As endotoxin is a potent mediator of inflammation, it may contribute to the aggravation of mucositis and, thus, co-treatment with an antiendotoxin compound (e.g., a Lipid A analog, such as eritoran) and antibiotics can be used as a more effective approach to treating oral mucositis in such patients, according to the invention.

The methods of the invention can also be used in conjunction with palliative therapies including the use of topical rinses, gels, or ointments that include lidocaine, articaine, and/or morphine, as well as other analgesic or anti-inflammatory agents. Specific examples of other agents and approaches that can be used in combination with TLR4 antagonists, according to the methods of the invention, include the following: palifermin (recombinant keratinocyte growth factor; rHuKGF; Kepivance™; Amgen) and AES-14 (uptake-enhanced L-glutamine suspension)(Peterson, J. Support Oncol. 4(2 Suppl. 1)9-13, 2006); oral cryotherapy, low-level laser therapy, chlorhexidine, amifostine, hematologic growth factors, pentoxifylline, and glutamine (Saadeh, Pharmacotherapy 25(4):540-554, 2005); amifostine, antibiotic paste or pastille, hydrolytic enzymes, ice chips, benzydamine, calcium phosphate, honey, oral care protocols, povidone, and zinc sulphate (Worthington et al., Cochrane Database Syst. Rev. 2:CD000978, 2006); flurbiprofen (e.g., administered as a tooth patch; Stokman et al., Support Care Cancer 13(1):42-48, 2005); diphenhydramine, magnesium hydroxide/aluminum hydroxide, nystatin, and corticosteroids (Chan et al., J. Oncol. Pharm. Pract. 11 (4):139-143, 2005); oral transmucosal fentanyl citrate (e.g., administered in the form of a lozenge; Shaiova et al., Support Care Cancer 12(4):268-273, 2004); clonazepam (e.g., in the form of a tablet; Gremeau-Richard et al., Pain 108(102):51-57, 2004); capsaicin (e.g., in the form of a lozenge; Okuno et al., J. Cancer Integr. Med. 2(3):179-183, 2004); ketamine (e.g., in the form of an oral rinse; Slatkin et al., Pain Med. 4(3):298-303, 2003); and granulocyte-macrophage colony-stimulating factor (GM-CSF)/granulocyte colony-stimulating factor (G-CSF), laser light therapy, and glutamine supplements (Duncan et al., Aliment. Pharmacol. Ther. 18(9):853-874, 2003).

The present invention is based, in part, on the following experimental results.

Example I

1. Introduction 1.1 Rationale

Two strains of C3H mice (C3H/HeJ and C3H/HeOuJ) differ from one another by the presence or absence of the LPS receptor TLR4 (present in the C3H/HeOuJ strain). C3H/HeJ mice are more sensitive to the lethal effects of total body radiation, but do not develop oral mucositis to the same extent as do the C3H/HeOuJ mice after a localized acute radiation to the snout. The mechanistic basis for these differences is not understood.

1.2 Acute Snout Radiation Model

The acute mouse snout radiation model in mice has been used to determine the radioprotective properties of experimental compounds. The course of oral mucositis in this model is well defined and results in peak mucositis 10-12 days following radiation. The acute model has little systemic toxicity, resulting in few radiation-induced animal deaths. In the present study, we used a dose of 30 Gy to induce oral mucositis.

2. Study Objective and Summary 2.1 Study Objective

The objective of the study described below was to evaluate the effect of localized acute radiation on the severity and duration of oral mucositis on two strains of mice. Wild type C3H/HeOuJ mice were compared to the endotoxin resistant strain C3H/HeJ. Mucositis was induced using an acute radiation dose of 30 Gy directed to the mouse snout. At several time points after radiation, groups of four mice of each strain were sacrificed. At the time of sacrifice, the tongues were removed and dissected into three pieces. The anterior third of each tongue was fixed in formalin for subsequent histological analysis. The middle third of each tongue was extracted to provide mRNA for analysis of cytokine expression levels. The posterior portion of each tongue was flash frozen in liquid nitrogen for future analysis. At the time of sacrifice, blood was taken from each animal and serum was prepared for subsequent cytokine analysis. This study focused on the pro-inflammatory cytokines TNF-α and IL-6.

2.2 Study Summary

A total of sixty-four (64) mice were used. Fifty-six (56) mice (28 each C3H/HeOuJ and 28 C3H/HeJ) were given a single dose of 30 Gy radiation directed to the snout on day 0. In addition, eight (8) mice (4 C3H/HeOuJ and 4 C3H/HeJ) were used as the no radiation control animals. Animals were sacrificed and blood and tissue taken according to the schedule described in Table 1.

according to a validated scale. Serum samples were assayed for the cytokines TNF-α and IL-6 using a standard ELISA assay.

4. Material and Methods 4.1 Animals

C3H/HeOuJ and C3H/HeJ mice (Jackson Laboratories), aged 5 to 6 weeks with body weights of 22.3 g, were used. Animals were individually numbered using an ear punch and housed in small groups of approximately 5 animals per cage. Animals were acclimatized prior to study commencement.

TABLE 1

Histological and cytokine comparison of the effects of ionizing radiation of the oral mucosa of C3H/HeJ and C3H/HeOuJ mice

| | Hour/Day | | | | | | | | | | | | | | | |
|---|---|---|---|---|---|---|---|---|---|---|---|---|---|---|---|---|
| | 0 | 2 H | 6 H | 1 | 2 | 3 | 4 | 5 | 6 | 7 | 8 | 9 | 10 | 11 | 12 | 13 | 14 |
| Randomize animals | X | | | | | | | | | | | | | | | | |
| Weigh, Record survival | X | | | X | X | X | X | X | X | X | X | X | X | X | X | X | X |
| Irradiate all animals 30 Gy to snout | X | | | | | | | | | | | | | | | | |
| Sacrifice 4 animals/group (1 and 2) dissect oral mucosa | | X | X | X | | X | | | X | | | | X | | | | X |
| Sacrifice 4 animals/group (3 and 4) dissect oral mucosa | | | | X | | | | | | | | | | | | | |
| Obtain serum from each animal | | X | X | X | | X | | | X | | | | X | | | | X |

3. Study Design

Sixty-four (64) mice (32 C3H/HeOuJ and 32 C3H/HeJ) were used. The mice were randomized into four (4) groups of either 28 animals (groups 1 and 2), the radiated groups, or 4 animals (groups 3 and 4), the un-irradiated control groups, as described in Table 2.

TABLE 2

Animal allocation by experimental group.

| Group | Mouse Strain | N | Radiation 30 Gy |
|---|---|---|---|
| 1 | C3H/HeOuJ WT | 28 | YES |
| 2 | C3H/HeJ Mutant | 28 | YES |
| 3 | C3H/HeOuJ WT | 4 | NO |
| 4 | C3H/HeJ Mutant | 4 | NO |

Every day for the period of the study (day 0 to day 14), each animal was weighed. Animals in groups 1 and 2 received a single dose of 30 Gy radiation focused on the snout on day 0. A lead shield protected the remainder of the animal body. At 2 hours, 6 hours, 24 hours (1 day), 3 days, 6 days, 10 days, and 14 days after radiation, 4 animals from groups 1 and 2 were sacrificed and blood and tissue were collected as described below. Animals in groups 3 and 4 were sacrificed, the tongues dissected, and blood collected on day 1. The tongues from each animal were dissected into 3 pieces (anterior, middle, and posterior) and each tongue was fixed in formalin. Mucositis was assayed by histological analysis of hematoxylin and eosin (H&E) stained sections of the formalin fixed tongues. Mucositis scoring was done in a blinded manner During this period of at least 2 days, the animals were observed daily in order to reject animals that presented in poor condition.

4.2 Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used, and was changed a minimum of once per week. Cages, tops, bottles, etc. were washed with a commercial detergent and allowed to air dry. Prior to use, these items were wrapped and autoclaved. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number, and treatment group was placed on all cages. The temperature and relative humidity was recorded during the study, and the records retained.

4.3 Diet

Animals were fed with a Labdiet® 5001 chow and water was provided ad libitum.

4.4 Animal Randomization and Allocations

Mice were randomly and prospectively divided into four (4) treatment groups prior to irradiation. Each animal was identified by an ear punch corresponding to an individual number. A cage card was used to identify each cage or label marked with the study number, treatment group number, and animal numbers.

4.5 Radiation

Machine calibration was checked within two weeks of the onset of the study. A single dose of radiation (30 Gy/dose) was administered to all animals in groups 1 and 2 on day 0. Radiation was generated with a 160 kilovolt potential (15-ma) source at a focal distance of 50 cm, hardened with a 0.35 mm Cu filtration system. Irradiation was done at a rate of 121.5 cGy/minute. Animals were anesthetized prior to radiation, and placed under lead shielding such that only the snout was exposed

4.6 Tissue and Blood Collection and Analysis

4.6.1 Animal Sacrifice and Tissue Collection

Animals in groups 3 and 4 were the un-irradiated control animals. The measurements from these animals provided a baseline control for all the irradiated samples in this study. The 4 animals in each of groups 3 and 4 were sacrificed on day 1.

Animals from groups 1 and 2 were sacrificed at several time points during the course of the study. At each time point, 4 animals per group were sacrificed. The time points were 2 hours, 6 hours, 24 hours, 3 days, 6 days, 10 days, and 14 days after radiation.

At the time of sacrifice, the tongues were removed and dissected into three pieces. The anterior third of each tongue was fixed in formalin for subsequent histological analysis. The middle third of each tongue was extracted to provide mRNA for analysis of cytokine expression levels. The posterior section of each tongue was flash frozen in liquid nitrogen and stored for future analysis.

At the time of sacrifice, approximately 1 mL of blood was taken from each animal and serum was prepared for subsequent cytokine analysis. This study focused on the pro-inflammatory cytokines TNF-$\alpha$ and IL-6.

4.6.2 Cytokine ELISA

Enzyme linked immunosorbent assays (ELISAs) were performed for cytokines TNF-$\alpha$ and IL-6 using kits purchased from R and D systems. These kits were used in accordance with the manufacturer's instructions. All determinations were made in duplicate on serum samples stored at −80° C. If insufficient serum had been collected to run both IL-6 and TNF-$\alpha$, samples were diluted 1:2 or 1:4, and run in duplicate in both assays. All assays were performed using 50 µL of sample per well.

4.6.3 Histology

Histological samples were fixed in 10% formaldehyde in saline and process for paraffin histology using standard techniques. Slides were stained with hematoxylin and eosin (H&E) and reviewed by a board certified pathologist.

4.7 Assessment of Results

Statistical differences between treatment groups were determined using One Way ANOVA. Body weights were evaluated for differences between the treatment groups.

5. Results and Discussion

5.1 Survival

A total of 6 deaths occurred on day 10. These were equally distributed between the C3H/HeOuJ and C3H/HeJ groups (3 deaths in each group) and, as a result of this, only one animal in each group was sacrificed on day 14. Additional animals were subsequently irradiated in order to provide additional animals to provide data for the day 14 time-point.

Figure 2:
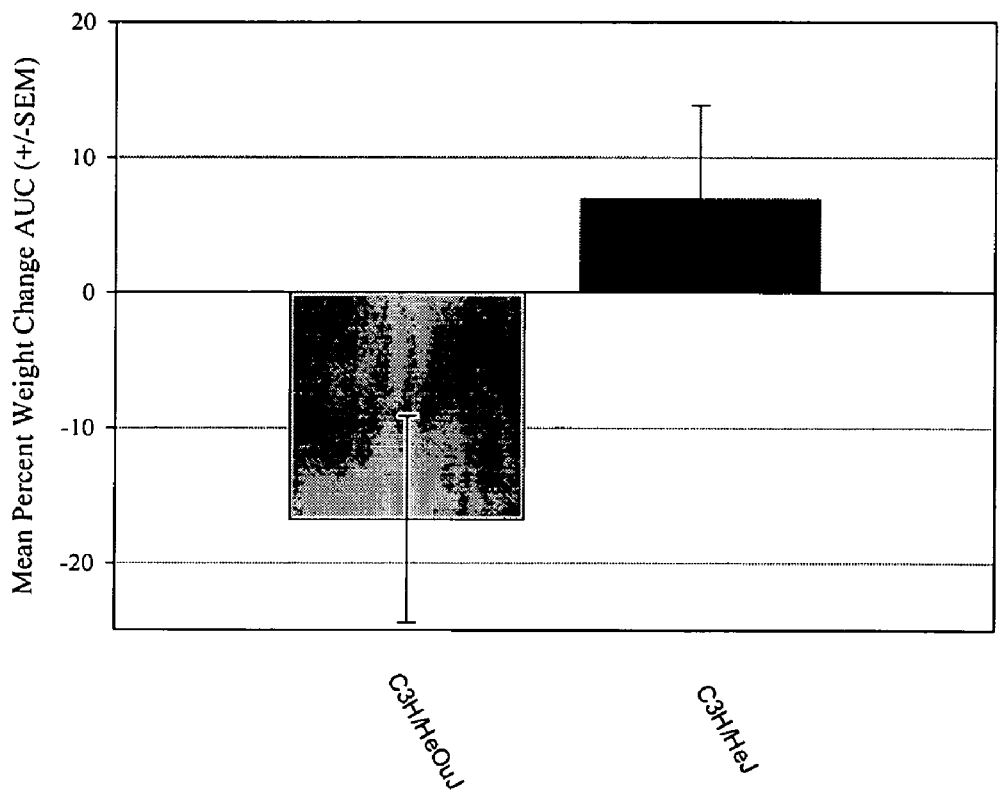
FIG. 2 is a graph showing the area under the curve (AUC) calculated for the percent weight change exhibited by snout irradiation-treated C3H/HeOuJ and C3H/HeJ mice. This calculation was made using the trapezoidal rule transformation. Group means were calculated and are shown with error bars representing SEM for each group. A one-way Anova test showed a statistically significant difference between the groups (P=0.008).

5.2 Weights (FIGS. 1 and 2)

The mean percentage weight change for each group is shown in FIG. 1. The weight change data show that both groups of animals lost approximately 5% of their starting body weight by day post irradiation, then gained weight until day 6. From day 6 until day 13, the C3H/HeJ mice maintained their weight between no gain and 5% increase relative to their starting weight. The C3H/HeOuJ lost approximately 10% of their body weight between days 7 and 9, and did not gain weight before day 13. To evaluate the differences between the two groups, the area under the curve (AUC) for each individual animal was calculated and the differences were evaluated using a One-Way ANOVA analysis. The mean AUC data is shown in FIG. 2. The One-Way ANOVA analysis showed that there was a statistically significant difference between the groups (P=0.008).

5.3 Serum Cytokine Levels

Serum levels of cytokines IL-6 and TNF-$\alpha$ were evaluated by ELISA.

5.3.1 Serum IL-6 Concentrations

Figure 3:
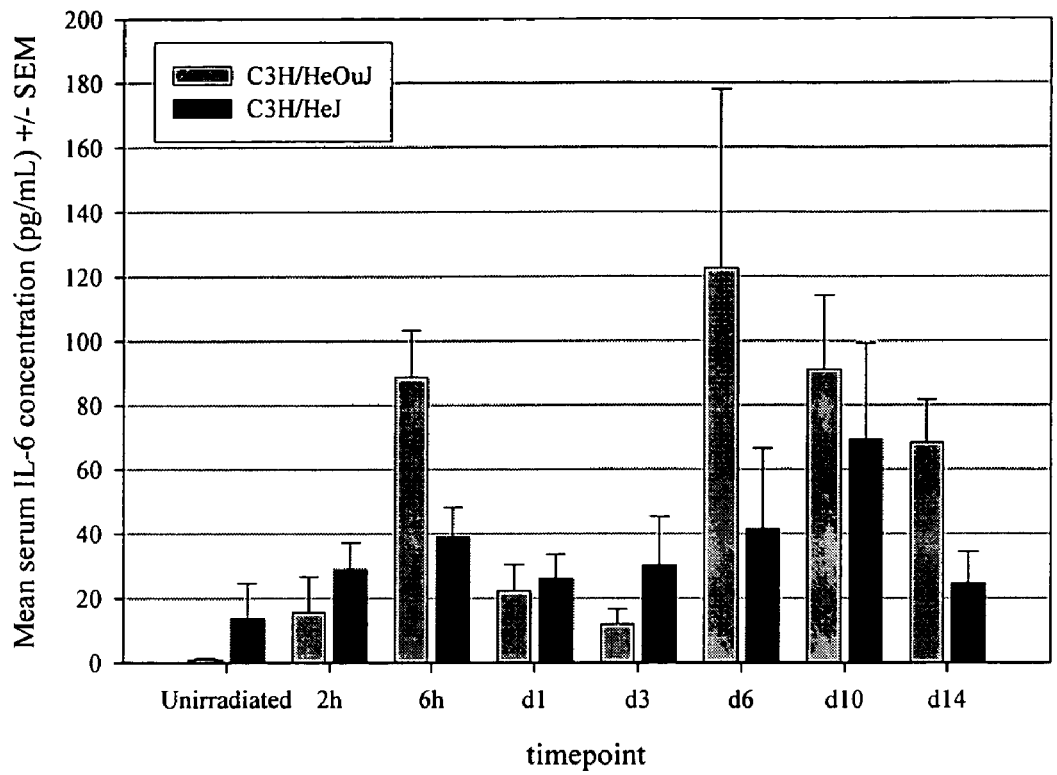
FIG. 3 is a graph showing the mean serum IL-6 concentration of snout irradiation-treated C3H/HeOuJ and C3H/HeJ mice measured by ELISA analysis at the indicated time points.

In un-irradiated C3H/HeOuJ mice, the mean serum concentration of IL-6 was 1.0 pg/mL. This level increased to 88.8 pg/mL at 6 hours post radiation, before falling to 12.0 pg/mL on day 3 following radiation and increasing to a peak level of 122.7 pg/mL on day 6. Days 10 and 14 showed a gradual decline from the peak levels seen on day 6. In un-irradiated C3H/HeJ mice, the mean serum concentration of IL-6 was 13.8 pg/mL. All other readings were between 25 and 42 pg/mL with the exception of the day 10 time-point, when serum IL-6 concentrations increased to 69.4 pg/mL. These data are shown in FIG. 3.

5.3.2 Serum TNF-$\alpha$ Concentrations

Figure 4:
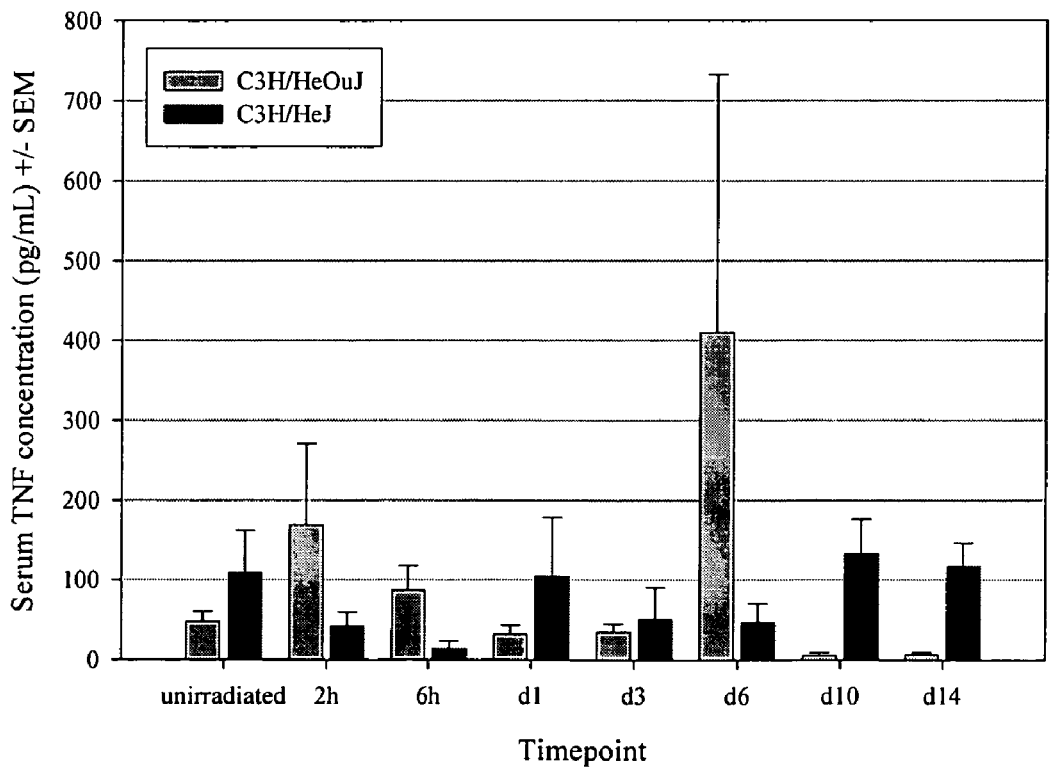
FIG. 4 is a graph showing the mean serum TNF-α concentration of snout irradiation-treated C3H/HeOuJ and C3H/HeJ mice measured by ELISA analysis at the indicated time points.

The mean serum TNF-$\alpha$ concentration in un-irradiated C3H/HeOuJ mice was 48.0 pg/mL. There were 2 peaks in serum TNF-$\alpha$ levels in these mice, one after 2 hours (168.7 pg/mL) and one at day 10 (410.2 pg/mL). At time-points between these 2 peaks, serum TNF-$\alpha$ concentrations were close to the levels seen in un-irradiated C3H/HeOuJ mice (31.6 pg/mL to 87.2 pg/mL). On days 10 and 14, the levels were lower than in the un-irradiated controls (5.7 pg/mL and 6.6 pg/mL respectively). In C3H/HeJ mice, un-irradiated control mice had mean serum TNF-$\alpha$ concentrations of 109.3 pg/mL. Subsequent post-irradiation readings were generally lower than this, ranging from 14.2 pg/mL at 6 hours post radiation to 133.8 pg/mL on day 10. These data are shown in FIG. 4.

5.4 Tongue Histology

Parts of each tongue were processed for routine hematoxylin and eosin (H&E) histology. These slides were then reviewed by a board certified pathologist and scored for epithelial and connective tissue pathology on a scale of 0-3, epithelial mitoses, percent ulceration, skeletal muscle damage, number of inflammatory cells per 10 high powered fields (including differential cell type analysis), and the number of small, medium, and large blood vessels.

5.4.1 Histological Score

Figure 5:
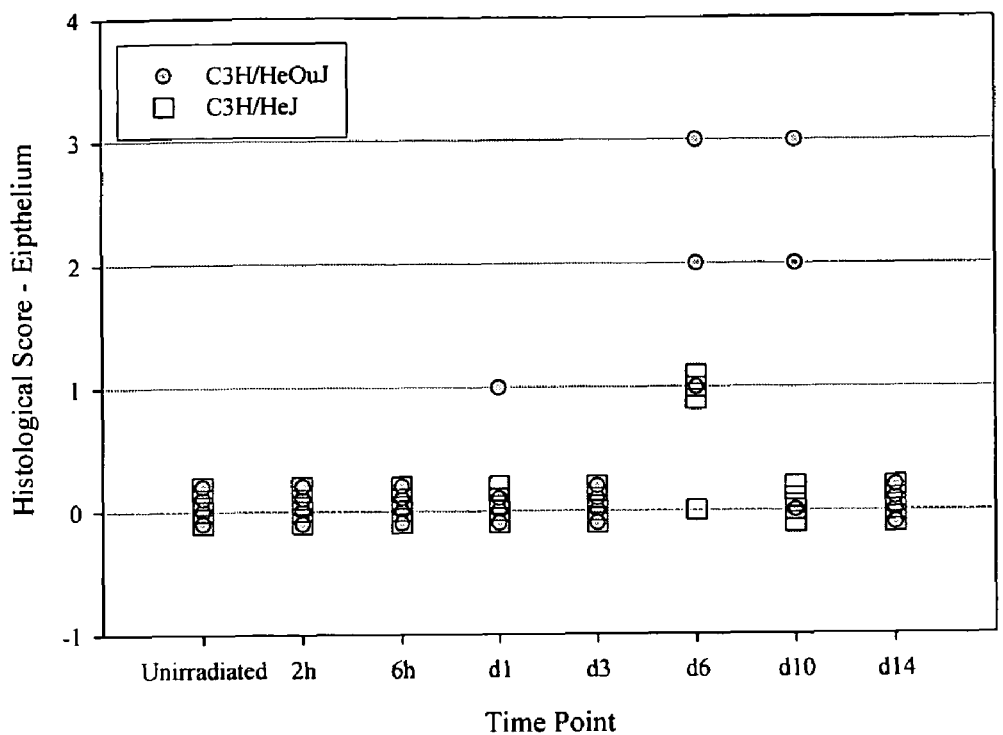
FIG. 5 is a graph of epithelial histology scores for snout irradiation-treated C3H/HeOuJ and C3H/HeJ mice. Each sample was scored on a scale of 0-3 for epithelial cell layer damage.
Figure 6:
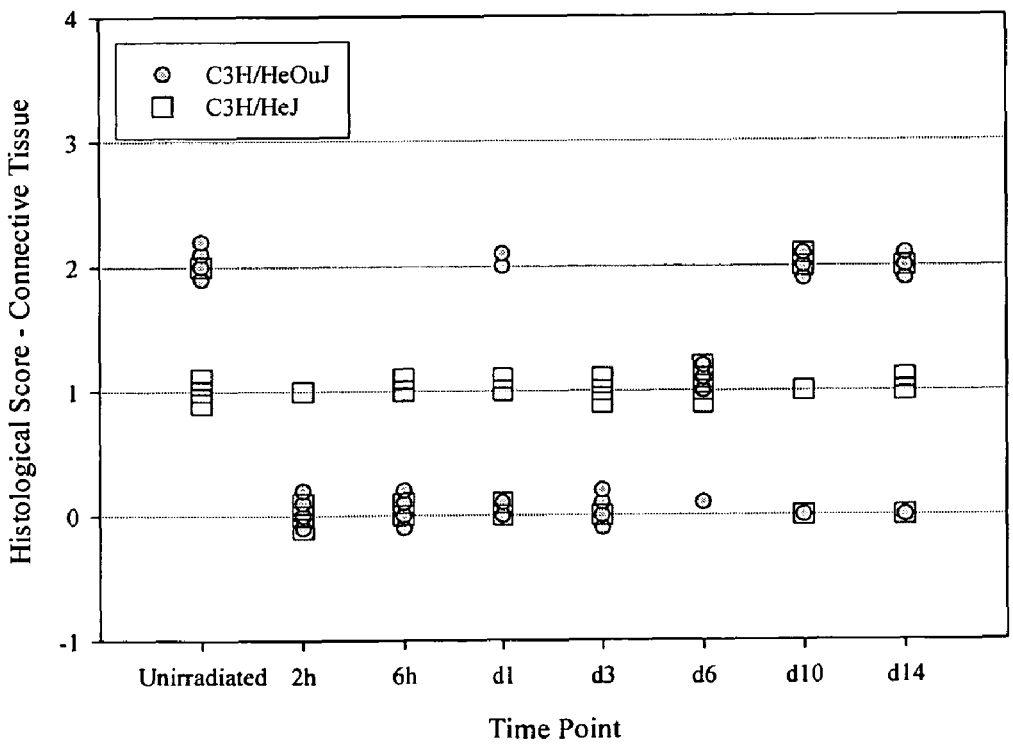
FIG. 6 is a graph of connective tissue histology scores for snout irradiation-treated C3H/HeOuJ and C3H/HeJ mice. Each sample was scored on a scale of 0-3 for connective tissue damage.

The epithelium and connective tissue regions of each sample were each given separate scores. The scores for the epithelium are shown in FIG. 5. The mean epithelial histological score for C3H/HeOuJ mice that had not been irradiated was 0, and this was also the case for all post-radiation time points except day 1, when the mean score was 0.25, and days 6 and 10, when the mean score was 2. In C3H/HeJ mice, the mean epithelial histological score was 0 at all time points except day 6, when the score was 0.75. The data for the mean connective tissue histological scores is shown in FIG. 6. The mean connective tissue histological score for C3H/HeOuJ mice that had not been irradiated was 2. This score dropped to 0 at 2 hours post-radiation, increased to a score of 1 on day 1 post radiation, before dropping to 0 on day 3 and increasing to 1.5 on days 10 and 14. In C3H/HeJ mice, the mean epithelial histological score was 1.25 in mice that had not been irradiated, dropping to 0.25 at 2 hours post radiation before increasing gradually to 1.25 on day 10. In the connective tissue, the histological score was as high or higher in the control un-irradiated mice than at any time following radiation, in both C3H/HeOuJ and C3H/HeJ mice. The reasons for this are currently unknown.

5.4.2 Inflammation

Figure 7:
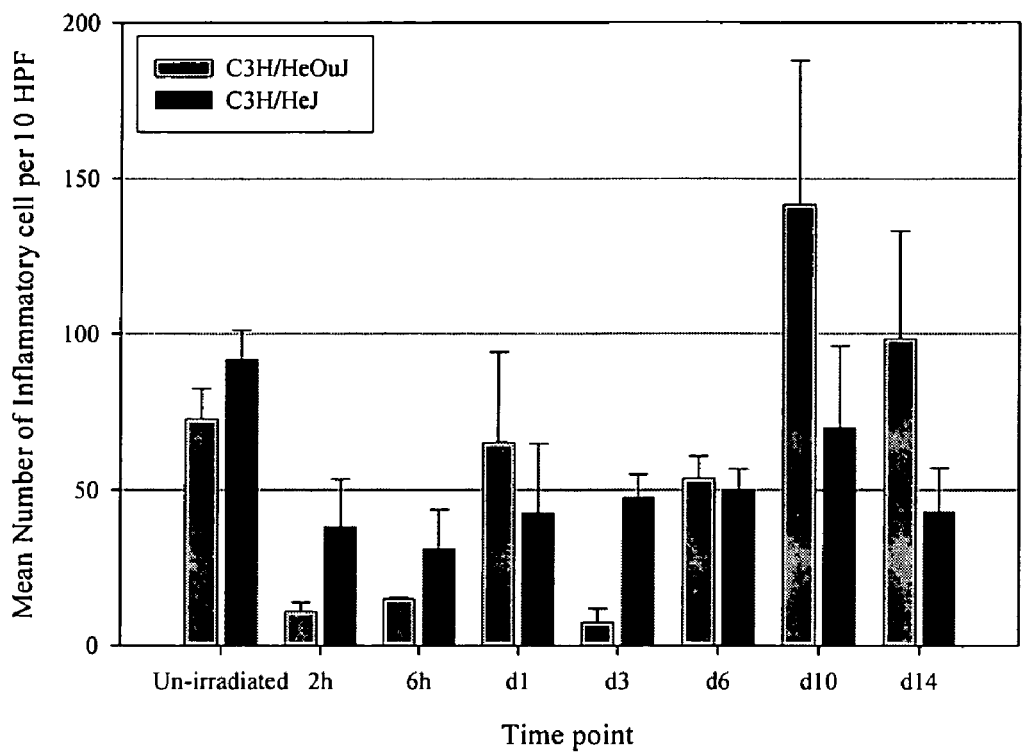
FIG. 7 is a graph showing the mean numbers of inflammatory cells of snout irradiation-treated C3H/HeOuJ and C3H/HeJ mice measured at the indicated time points.

The mean number of inflammatory cells per ten high powered fields for each strain of mouse at each time point was calculated and the results are shown in FIG. 7. The numbers of cells seen in the connective tissue of un-irradiated animals was higher than expected in both strains of mice, and was lower at all post irradiation time-points in the C3H/HeJ mice. In the C3H/HeOuJ mice, the numbers of inflammatory cells seen at most time points was also lower than those observed in un-irradiated controls, except for day 10, when the number of cells was approximately 2 times higher than the un-irradiated controls (and about 10 times higher than the 2 hour and 6 hour time-points) and on day 14, when the numbers observed were about 50% higher than the un-irradiated controls. As for the connective tissue histology scores, the reasons for the unexpectedly high numbers seen in the un-irradiated animals are unknown. In all cases, the bulk of the infiltrate was composed of lymphocytes, with monocytes and macrophage accounting for almost all of the non-lymphocytic cells most animals. Significant numbers of polymorphonucleocytes (PMNs or neutrophils) were only seen in three animals from the day 10 time-point (1 OuJ and 2 HeJ).

5.4.3 Epithelial Cell Mitoses

Figure 8:
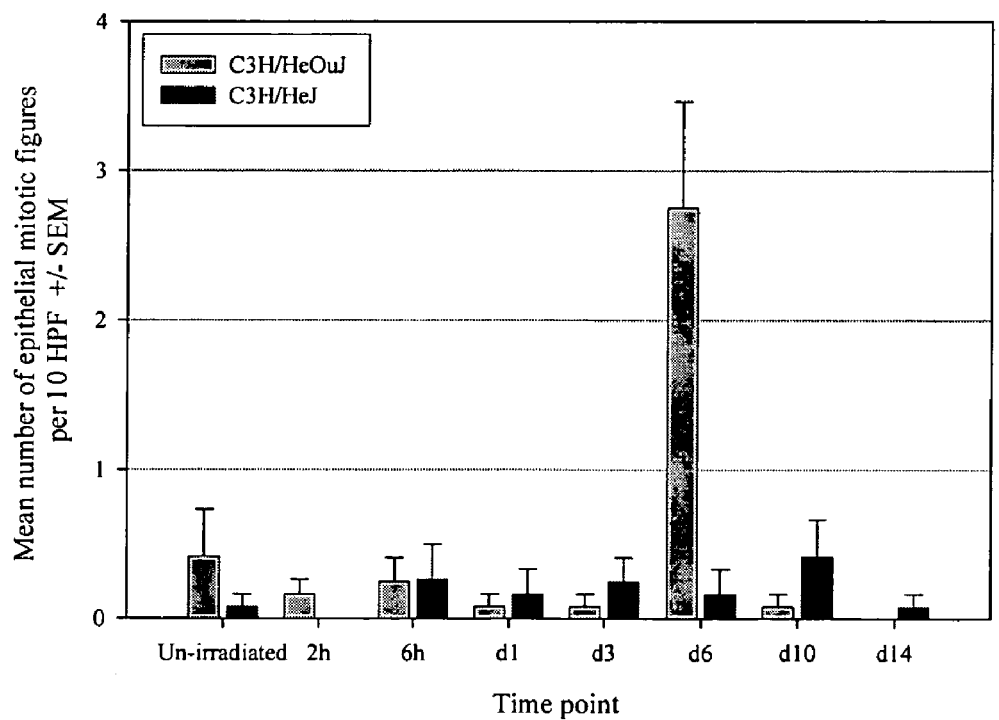
FIG. 8 is a graph showing the mean numbers of mitoses in the epithelial cell layer of snout irradiation-treated C3H/HeOuJ and C3H/HeJ mice measured at the indicated time points.

The number of mitotic figures seen in the epithelial cell layer was counted and the mean number of mitoses per ten high power fields for each strain at each time point is shown in FIG. 8. The number of mitotic figures counted in the epithelial cell layer of C3H/HeOuJ mouse tongues was generally low, with a mean of 0.4 in un-irradiated mice and numbers lower than this at all time points except day 6, when a mean of 2.75 was observed. In C3H/HeJ mice the numbers of mitoses seen in un-irradiated mice was lower than in C3H/HeOuJ mice with a mean of 0.1. However, this increased to 0.4 by day 10 post radiation.

5.4.4 Blood Vessels

Figure 9:
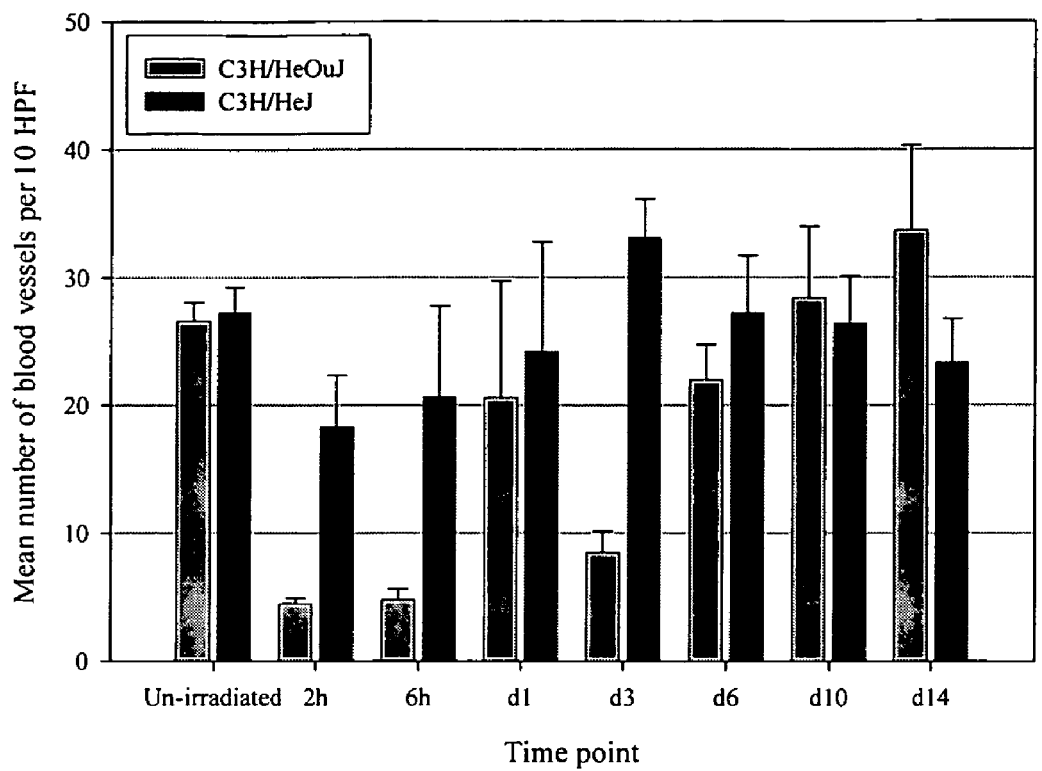
FIG. 9 is a graph showing the mean numbers of blood vessels per 10 high power fields of snout irradiation-treated C3H/HeOuJ and C3H/HeJ mice measured at the indicated time points.
Figure 10:
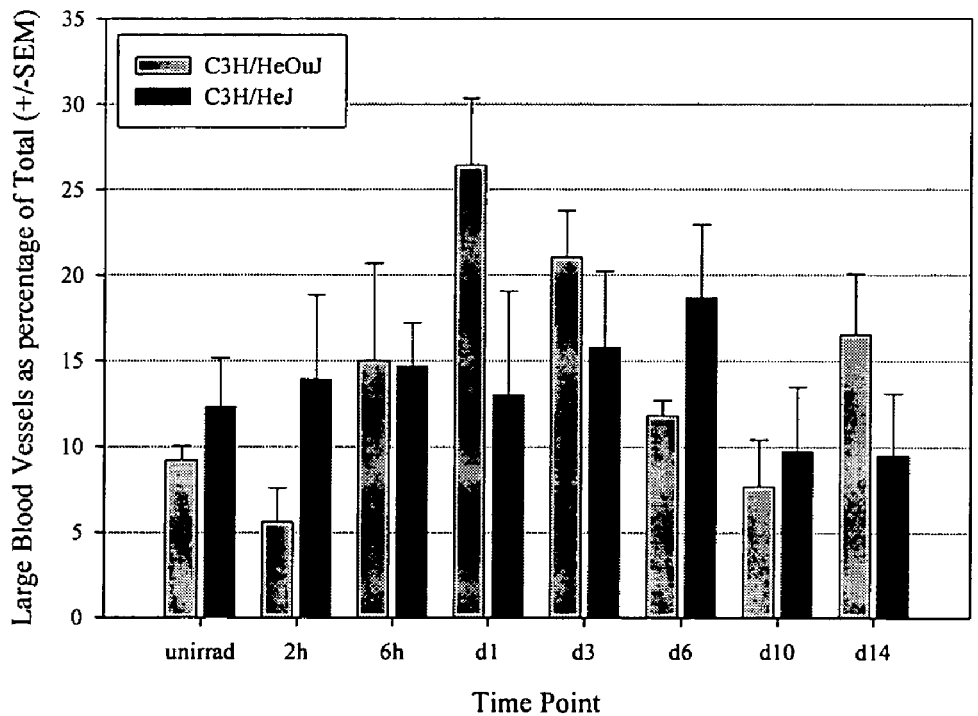
FIG. 10 is a graph showing the mean number of large blood vessels as a percentage of total blood vessels per 10 high power fields for C3H/HeOuJ and C3H/HeJ mice measured at the indicated time points. The values are expressed as a percentage of the total numbers of blood vessels observed in those fields.

The number of blood vessels per ten high power fields was counted for each sample and the mean number for each strain of mouse at each time point calculated. These data are shown in FIG. 9. The number of blood vessels per 10 high power fields was 26.6 in un-irradiated C3H/HeOuJ mice and 27.2 in un-irradiated C3H/HeJ mice. In C3H/HeOuJ mice, the number of blood vessels had apparently dropped to 4.5 by 2 hours post radiation, rising to 20.6 on day 1, before falling to 8.5 on day 3, and increasing on days 6 and 10, before reaching a peak of 33.7 on day 14. This represents an increase of 27% relative to the un-irradiated controls and 648% relative to the 2 hour time point. It is interesting to note that the un-irradiated control animals, sacrificed on day 1, have similar levels to the day 1 time-point. In the C3H/HeJ mice, the number of blood vessels was generally close to the un-irradiated controls, reaching a minimum of 18.3 at 2 hours post radiation, and a maximum of 33.1 on day 6 post radiation. To evaluate the qualitative changes in the blood vessels, the numbers of large blood vessels per 10 high power fields were evaluated and the resulting numbers expressed as a percentage of the total number of vessels seen in the same 10 high power fields. The results of this analysis are shown in FIG. 10 and indicate that the number of large blood vessels seen in the C3H/HeOuJ mice increased from a mean of 9.2% in the un-irradiated control mice, to a peak of 26.5% on day 1 (24 hours post radiation), and declined during the remainder of the study. The C3H/HeJ mice had a slightly higher control level of 13.2% in the un-irradiated mice, which increased to a peak of 18.7% on day 6 post radiation, and fell to levels below controls on days 10 and 14 post radiation.

6. Conclusions

1. C3H/HeOuJ mice showed greater weight loss than the C3H/HeJ mice during this study, and the differences observed were statistically significant when evaluated with a one-way ANOVA test (P=0.008).

2. Analysis of serum cytokine levels showed that the un-irradiated C3H/HeJ control mice had higher levels than their C3H/HeOuJ counterparts, but that the C3H/HeOuJ mice showed greater increases in serum cytokines following radiation than C3H/HeJ, with peak levels of both IL-6 and TNF-$\alpha$ being seen on day 6 post irradiation.

3. Histologically, very little change was seen in C3H/HeJ mice. C3H/HeOuJ mice showed a significant disturbance of the epithelium on days 6 and 10 following radiation. Histological scores for the connective tissue were high in the un-irradiated control C3H/HeOuJ mice and declined at 2 hours to 6 days post radiation, returning to near control levels at days 10 and 14 post radiation.

4. The numbers of inflammatory cells present showed little change in the C3H/HeJ mice but increased to a peak on day 10 post radiation in C3H/HeOuJ mice, coinciding with the tissue peak tissue cytokine levels in these animals. Infiltrates were predominantly lymphocytic in nature.

5. The number of mitoses observed in the epithelial cell layer showed a slight increase in C3H/HeJ mice, peaking on day 10, while a significant spike in mitotic activity was noted on day 6 in the C3H/HeOuJ mice.

6. In the analysis of the number and size of blood vessels observed, few changes were noted in the C3H/HeJ mice, while the C3H/HeOuJ mice showed a decrease in the number of blood vessels immediately following radiation (2 and 6 hours post radiation), combined with an overall increase at the later time points (days 10 and 14 post radiation). An increase in the percentage of large blood vessels was noted 24 hours post radiation in C3H/HeOuJ mice.

Example II

1. Introduction 1.1 Rationale

As noted above in Example I, two strains of C3H mice (C3H/HeJ and C3H/HeOuJ) differ from one another by the presence or absence of the LPS receptor TLR4 (present in the C3H/HeOuJ strain). In the experiments described above, it is established that the C3H/HeOuJ strain is susceptible to oral mucositis induced by focal radiation to the snout, while the C3H/HeJ strain is relatively resistant to radiation induced mucositis. Evaluation of the pro-inflammatory cytokines in these animals showed that the induction of these cytokines via the LPS receptor TLR4 in the C3H/HeOuJ mice may play a role in the development of oral mucositis. The purpose of the study described below was to evaluate a compound that blocks stimulation of TLR4 (eritoran) in the murine model of oral mucositis.

1.2 Acute Snout Radiation Model

The acute mouse snout radiation model in mice has been used to determine the radio-protective properties of experimental compounds. The course of oral mucositis in this model is well defined and results in peak mucositis 10-12 days following radiation. The acute model has little systemic toxicity, resulting in relatively few radiation induced animal deaths. In this study, a dose of 30 Gy was used to induce oral mucositis.

2. Study Objective and Summary 2.1 Study Objective

The objective of the study described below was to examine the effects of eritoran administered subcutaneously on the severity and duration of oral mucositis induced by radiation. Mucositis is induced using an acute radiation dose of 30 Gy directed to the mouse snout. At several time points after radiation, groups of four mice from each treatment group were sacrificed. At the time of sacrifice, the tongues were removed and dissected into three pieces. The anterior third of each tongue was fixed in formalin for subsequent histological analysis. The middle third of each tongue was extracted to provide mRNA for analysis of cytokine expression, and the posterior portion of each tongue was flash frozen in liquid nitrogen and stored for future analysis. At the time of sacrifice, blood was taken from each animal and serum was prepared for subsequent cytokine analysis.

2.2 Study Summary

A total of fifty-four (54) animals were used in this study. Forty-eight (48) C3H/HeOuJ mice were divided into 3 groups of 16 animals per group (groups 1-3). An additional 6 animals were put into a separate control group (group 4) as described in Table 2.

3. Study Design

Fifty-four (54) male C3H/HeOuJ mice aged 6-7 weeks and weighing approximately 22 g were used. There were three (3) treatment groups of sixteen (16) animals each, and a control group of six (6) animals that received no radiation. All animals had a jugular cannula inserted into the left jugular vein on day −3. Beginning on day 0, animals in groups 1 and 4 were dosed twice a day by injection via cannula with placebo. Animals in group 2 were dosed with 2 IV injections of eritoran at 1 mg/kg daily, starting 2 hours or less before radiation on day 0 and continuing until day 10. Animals in group 3 were dosed with 2 IV injections of eritoran at 10 mg/kg daily, starting 2 hours or less before radiation on day 0 and continuing until day 10. Animals in groups 1, 2, and 3 were given a single dose of 30 Gy radiation directed to the snout on day 0. The 6 animals in group 4 were used as the no radiation control animals (see Table 2). Eight animals in each of groups 1, 2, and 3 were sacrificed and blood and tissue taken according to the schedule described in Table 2.

TABLE 2

Allocation by experimental group.

| Group | Number of animals | Strain | Treatment | Radiation | Sac points |
|---|---|---|---|---|---|
| 1 | 16 male | C3H/HeOuJ | placebo IV bid | 30 Gy to snout | 8 on day 6, 8 on day 10 |
| 2 | 16 male | C3H/HeOuJ | eritoran 1 mg/kg IV bid | 30 Gy to snout | 8 on day 6, 8 on day 10 |
| 3 | 16 male | C3H/HeOuJ | eritoran 10 mg/kg IV bid | 30 Gy to snout | 8 on day 6, 8 on day 10 |
| 4 | 6 male | C3H/HeOuJ | placebo IV bid | none | 6 on day 10 |

4. Material and Methods 4.1 Animals

C3H/HeOuJ mice (Jackson Laboratories), aged 5 to 6 weeks with body weight of 21.3 g, were used. Animals were individually numbered using an ear punch and individually housed. Animals were acclimatized prior to study commencement. During this period of at least 2 days, the animals were observed daily in order to reject animals that presented in poor condition.

4.2 Housing

The study was performed in animal rooms as described above in section 4.2 of Example I.

4.3 Diet

Animals were fed with Labdiet® 5061 sterile irradiated rodent chow and water was provided ad libitum.

4.4 Animal Randomization and Allocations

Mice were randomly and prospectively divided into three (3) treatment groups prior to irradiation. Each animal was identified by an ear punch corresponding to an individual number. A cage card was used to identify each cage or label marked with the study number, treatment group number, and animal numbers.

4.5 Radiation

Machine calibration was checked within two weeks of the onset of this study. A single dose of radiation (30 Gy/dose) was administered to all animals in groups 1 and 2 on day 0. Radiation was generated with a 160 kilovolt potential (15-ma) source at a focal distance of 50 cm, hardened with a 0.35 mm Cu filtration system. Irradiation was done at a rate of 121.5 cGy/minute. Animals were anesthetized prior to radiation, and placed under lead shielding such that only the snout is exposed 4.6 Tissue Collection and Analysis 4.6.1 Histology Histological samples were fixed in 10% formaldehyde in saline and process for paraffin histology using standard techniques. Slides were stained with hematoxylin and eosin (H&E).

4.7 Assessment of Results

Statistical differences between treatment groups were determined using One Way ANOVA. Body weights were evaluated for differences between the treatment groups.

5. Results and Discussion

Figure 11:
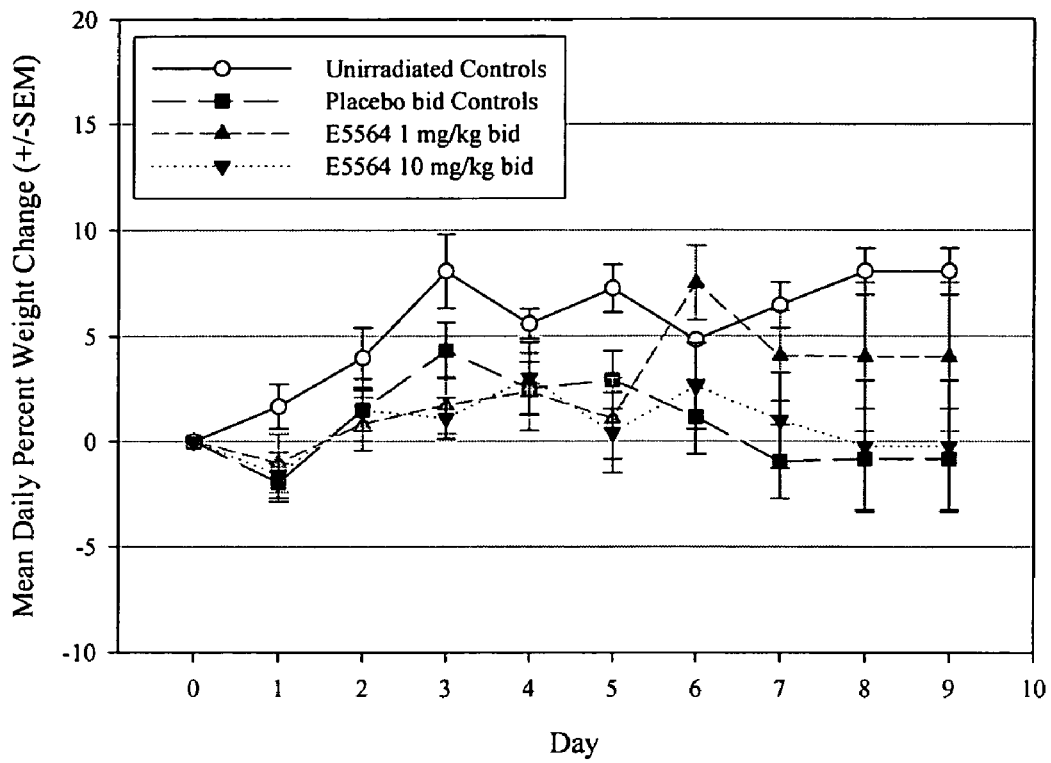
FIG. 11 is a graph showing percent weight change of C3H/HeOuJ mice treated with the indicated amounts of eritoran, after snout irradiation treatment. The animals were weighed daily, the percent weight change from day 0 was calculated, and group means and standard errors of the mean (SEM) calculated for each day.
Figure 12:
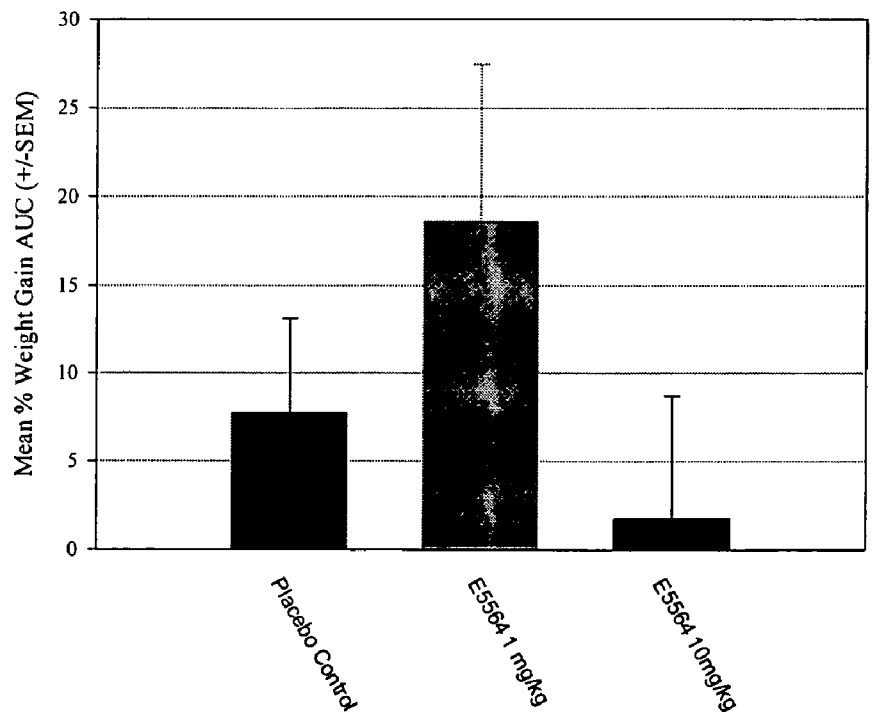
FIG. 12 is graph showing the area under the curve (AUC) calculated for the percent weight change exhibited by snout irradiation-treated C3H/HeOuJ mice shown in FIG. 11. This calculation was made using the trapezoidal rule transformation. Group means were calculated and are shown with error bars representing SEM for each group. A one-way Anova test showed no statistically significant differences between groups (P=0.261).

5.1 Weights (FIGS. 11 and 12)

The mean percentage weight gain for each group for each day of the study is shown in FIG. 11. The un-irradiated control group gained an average of 8.1% during the study, as compared with a mean loss of 0.8% in the placebo group. In the groups receiving eritoran, a mean weight gain of 4.0% was seen in the group receiving 1 mg/kg as compared with a net loss of 0.2% in the group receiving 10 mg/kg. The results of this analysis for the three groups receiving radiation are shown in FIG. 12. There were no significant differences between these three groups (P=0.261). When compared against the un-irradiated controls, there were significant differences between the un-irradiated group and the radiated groups receiving placebo (P<0.001) and eritoran 10 mg/kg (P<0.001).

5.3 Tongue Histology

Each tongue was processed for routine hematoxylin and eosin histology. Because of several technical reasons, a total of 44 samples were evaluated. Of these 44 samples, 6 were in the un-irradiated control group, 12 were in the placebo group (6 each on days 6 and 10), 14 were in the eritoran 1 mg/kg treated group (7 each on days 6 and 10), and 12 were in the eritoran 10 mg/kg treated group (7 on day 6, and 5 on day 10).

The most common overall observation over the entire data set was normal or essentially normal. This was used in the description of 14 samples, 4 of which were in the un-irradiated control group. Normal was also used to describe 6 of the 14 samples in the 1 mg/mg eritoran treated group (2/7 samples from day 6 and 4/7 samples from day 10), and 3 of the 12 samples in the eritoran 10 mg/kg treated group (1/7 samples from day 6 and 2/5 samples from day 10). Only one of the 12 samples from the placebo treated group was described as normal (a day 6 sample). Hyperkeratosis was also seen in 14 of the samples, none of which were in the un-irradiated control group. Hyperkeratosis was most commonly seen in samples from the eritoran 10 mg/kg treated group, where it was applied to 7 of the 12 samples (3/7 at day 6 and 4/5 at day 10). Hyperkeratosis was seen in 5 of the 14 samples in the eritoran 1 mg/kg treated group (1/7 at day 6 and 4/7 on day 10). Only 2 samples in the placebo group were seen with hyperkeratosis, one at each time-point. Epithelial hyperplasia was seen in only 5 samples, however 4 of these samples were in the eritoran 10 mg/kg treatment group (2 at each time-point) and the fifth was in the placebo group (day 6). These observations seem to indicate a substantial improvement in both eritoran treatment groups relative to the placebo controls, with the high dose treatment group (10 mg/kg) showing a tendency to hyperplasia and hyperkeratosis.

Connective tissue damage or disruption was seen in a total of 11 samples, 8 of which were in the placebo treated group (3/6 on day 6 and 5/6 on day 10), 2 were in the eritoran 1 mg/kg treated group (both day 6), 1 was in the eritoran 10 mg/kg treated group (day 6). Loss or break in the epithelium was noted in 7 samples, and epithelial atrophy was noted in an additional 5 samples. Of these 12 samples with epithelial damage, 5 were in the placebo treated group (2 on day 6 and 3 on day 10), 5 were in the eritoran 1 mg/kg treated group (all on day 6), and 2 were in the eritoran 10 mg/kg group (both on day 6). Increased cellularity was seen in 10 samples, 2 in the placebo group (one each on day 6 and day 10), 5 in the eritoran 1 mg/kg treated group (one on day 6 and 4 on day 10), and 3 in the eritoran 10 mg/kg treated group (one on day 6 and 2 on day 10). Two types of infiltrate were observed, round cell or lymphocytic infiltrates were noted in 8 samples, were evenly distributed among the groups and time-points, and were seen in one of the 6 un-irradiated controls. Mast cell infiltrates were observed in 9 samples, 7 of which were in the placebo treated group (5 on day 6, and 2 on day 10), and the other 2 samples were in the eritoran 10 mg/kg treated group, day 6 time-point. The other observations regarding vasodilation and increased vascularity were evenly distributed or too rarely seen to show any meaningful differences between the treatment groups. These observations indicate that eritoran treatment results in improved tongue histology, as shown by decreased radiation-induced connective tissue damage and mast cell infiltration.

Figure 13:
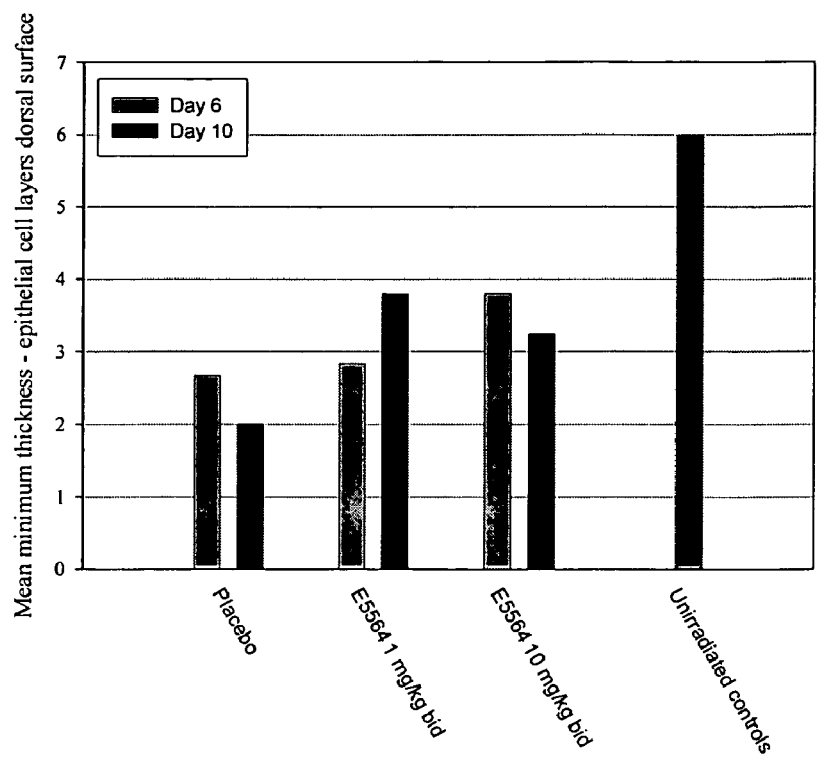
FIG. 13 is a graph showing the minimum number of epithelial cell layers on the dorsal surface of the tongue for snout irradiation-treated C3H/HeOuJ mice treated with the indicated amounts of eritoran, at the indicated timepoints.
Figure 14:
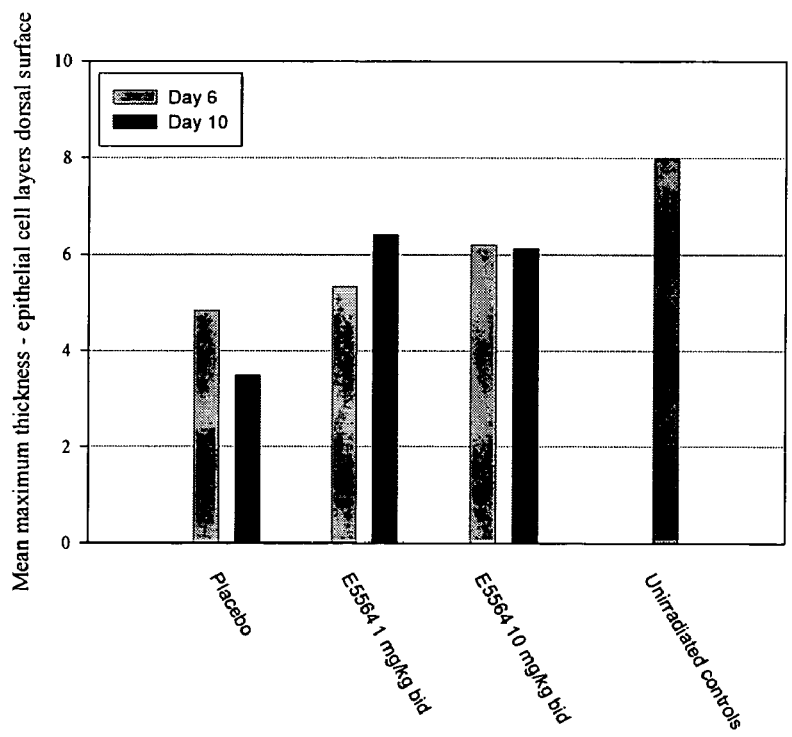
FIG. 14 is a graph showing the maximum number of epithelial cell layers on the dorsal surface of the tongue for snout irradiation-treated C3H/HeOuJ mice treated with the indicated amounts of eritoran, at the indicated timepoints.
Figure 15:
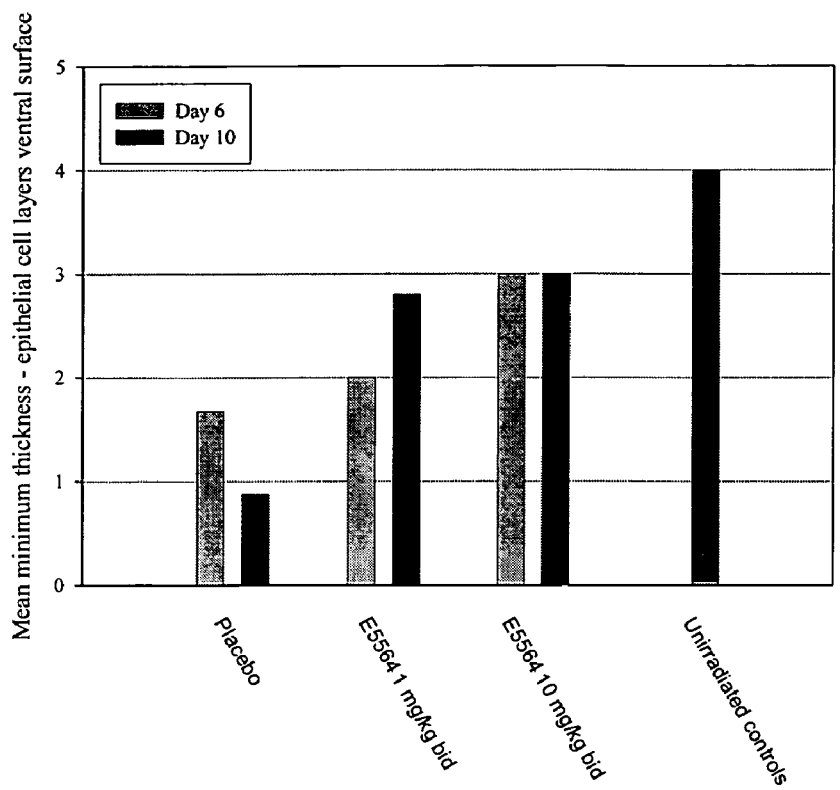
FIG. 15 is a graph showing the minimum number of epithelial cell layers on the ventral surface of the tongue for snout irradiation-treated C3H/HeOuJ mice treated with the indicated amounts of eritoran, at the indicated timepoints.
Figure 16:
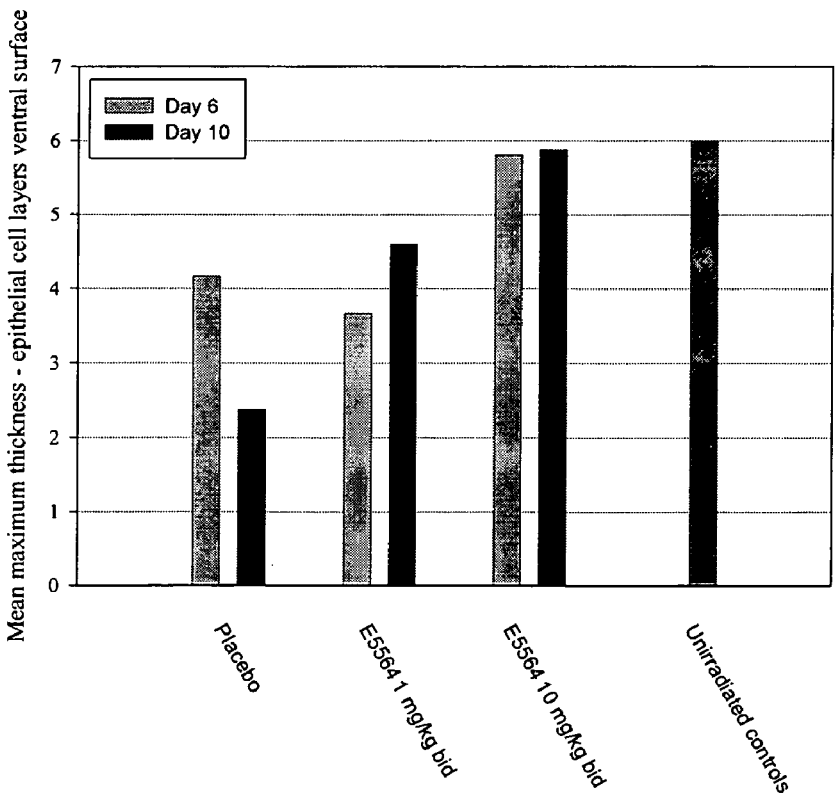
FIG. 16 is a graph showing the maximum number of epithelial cell layers on the ventral surface of the tongue for snout irradiation-treated C3H/HeOuJ mice treated with the indicated amounts of eritoran, at the indicated timepoints.

5.3.1 Thickness of the Epithelial Surface on the Dorsal and Ventral Surfaces of the Tongue Each sample was evaluated for the minimum and maximum number of epithelial cell layers on the dorsal and ventral surfaces of the tongue. From these numbers, mean minimum and maximum thickness was calculated for each treatment group at each time-point. For the dorsal surface of the tongue, the mean minimum number of cell layers in the un-irradiated controls was 6 cell layers. In the placebo control treatment group, the mean number of cell layers was 2.7 on day 6 and 2.0 on day 10. In the eritoran treated groups, the mean minimum number of cell layers was 2.8 (day 6) and 3.8 (day 10) in the 1 mg/kg group and 3.8 (day 6) and 3.3 (day 10) in the 10 mg/kg group. These data are shown in FIG. 13. The mean maximum number of epithelial cell layers on the dorsal surface in the un-irradiated controls was 8. In the placebo control treatment group, the mean number of cell layers was 4.8 on day 6 and 3.5 on day 10. In the eritoran treated groups, the mean minimum number of cell layers was 5.3 (day 6) and 6.4 (day 10) in the 1 mg/kg group, and 6.2 (day 6) and 6.1 (day 10) in the 10 mg/kg group. These data are shown in FIG. 14. On the ventral surface, the mean minimum number of cell layers in the un-irradiated controls was 4 cell layers. In the placebo control treatment group, the mean number of cell layers was 1.7 on day 6 and 0.9 on day 10. In the eritoran treated groups, the mean minimum number of cell layers was 2.0 (day 6) and 2.8 (day 10) in the 1 mg/kg group, and 3.0 (day 6 and day 10) in the 10 mg/kg group. These data are shown in FIG. 15. The mean maximum number of epithelial cell layers on the ventral surface in the un-irradiated controls was 6. In the placebo control treatment group, the mean number of cell layers was 4.2 on day 6 and 2.4 on day 10. In the eritoran treated groups, the mean minimum number of cell layers was 3.7 (day 6) and 4.6 (day 10) in the 1 mg/kg group and 5.8 (day 6) and 5.9 (day 10) in the 10 mg/kg group. These data are shown in FIG. 16. These observations indicate that eritoran seems to protect the epithelial cell layer, with the 10 mg/kg group showing slightly greater protection that the 1 mg/kg group, particularly on the ventral surface.

6. Conclusions

1. Significant mortality was seen during this study, but this excess mortality was not associated with any one treatment group.
2. No statistically significant differences in weight gain were seen between the three irradiated treatment groups.
3. Both groups treated with eritoran showed improvement in tongue histology relative to the placebo treated control group, as determined by the number of samples described as normal, increases in epithelial hyperplasia and hyperkeratosis, and decreases in connective tissue damage and mast cell infiltrates.

4. Although both groups treated with eritoran showed improvements in tongue histology, there were distinct differences in the descriptive histology between the 1 mg/kg and 10 mg/kg groups, although it is not clear which dose showed the greater improvement.

Example III

1. Introduction 1.1 Rationale

As discussed above, two strains of C3H mice (C3H/HeJ and C3H/HeOuJ) differ from one another by the presence or absence of the LPS receptor TLR4 (present in the C3H/HeOuJ strain), and the C3H/HeOuJ strain are susceptible to oral mucositis induced by focal radiation to the snout, while the C3H/HeJ strain are relatively resistant to radiation induced mucositis. Further as described above, evaluation of the pro-inflammatory cytokines in these animals shows that the induction of these cytokines via the LPS receptor (TLR4) in the C3H/HeOuJ mice may play a role in the development of oral mucositis. The experiments described in Example II demonstrated the efficacy of eritoran in a model of oral mucositis. The study described below identifies optimal dosing schedules for eritoran.

1.2 Acute Snout Radiation Model

The acute mouse snout radiation model has been used to determine the radio-protective properties of experimental compounds. The course of oral mucositis in this model is well defined and results in peak mucositis 10-12 days following radiation. The acute model has little systemic toxicity, resulting in relatively few radiation induced animal deaths. In this study, a dose of 30 Gy was used to induce oral mucositis.

2. Study Objective and Summary 2.1 Study Objective

The objective of this study was to examine the effect of scheduling of eritoran, administered intraveneously, on the severity and duration of oral mucositis induced by radiation. Mucositis was induced using an acute radiation dose of 30 Gy directed to the mouse snout. At 10 days after radiation, groups of four mice from each treatment group were sacrificed. At the time of sacrifice, the tongues were removed and fixed in formalin for subsequent histological analysis. At the time of sacrifice, blood was taken from each animal and serum was prepared for subsequent cytokine analysis. These samples were used for the measurement of serum Tumor Necrosis Factor (TNF-α), Interleukin-6 (IL-6), and Serum Amyloid A (SAA) levels.

2.2 Study Summary

Sixty (60) C3H/HeOuJ mice were obtained from Jackson Laboratories. These animals were shipped with jugular cannulae already implanted. The animals were randomly divided into 6 groups of 10 animals per group as described in Table 4.

3. Study Design

Sixty (60) male C3H/HeOuJ mice aged 6-7 weeks and weighing approximately 22 g were used. There were five (5) treatment groups of ten (10) animals each, and a control group of ten (10) animals, which received no radiation. Beginning on day 0, 2 hours or less before radiation, animals in groups 1-6 were dosed with either placebo or eritoran 10 mg/kg as detailed in Table 4. Dosing continued twice daily from the day of radiation (day 0) until day 9. Animals in groups 1 and 2 received placebo throughout the dosing period. Animals in group 3 received eritoran at 10 mg/kg for the entire dosing period. Animals in group 4 received eritoran at 10 mg/kg twice daily from day 0 until day 3, and then placebo twice daily until the end of the dosing period. Animals in group 5 received placebo twice daily from day 0 until day 2, then eritoran 10 mg/kg twice daily from day 3 until day 6, and then placebo twice daily until the end of the dosing period. Animals in group 6 received placebo twice daily from day 0 until day 5, then eritoran 10 mg/kg twice daily until the end of the dosing period. All drug and placebo administration was via intravenous via jugular cannula.

TABLE 4

Allocation by experimental group

| Group | Number of Animals | Treatment | Eritoran | Placebo | Dose Volume |
|---|---|---|---|---|---|
| 1 | 10 Male | No Radiation Placebo | | Days 0-9 | 0.1 mL |
| 2 | 10 Male | Placebo | | Days 0-9 | 0.1 mL |
| 3 | 10 Male | eritoran days 0-9 10 mg/kg bid | Days 0-9 | | 0.1 mL |
| 4 | 10 Male | eritoran days 0-3 10 mg/kg bid | Days 0-3 | Days 4-9 | 0.1 mL |
| 5 | 10 Male | eritoran days 3-6 10 mg/kg bid | Days 3-6 | Days 0-2 & Days 7-9 | 0.1 mL |
| 6 | 10 Male | eritoran days 6-9 10 mg/kg bid | Days 6-9 | Days 0-5 | 0.1 mL |

Every day for the period of the study (day 0 to day 10), each animal was weighed to an accuracy of 0.1 g. At 10 days after radiation, all animals were sacrificed and the tongues taken for histological analysis. Blood was taken at the time of sacrifice and serum was stored at −80° C.

4. Material and Methods 4.1 Animals

C3H/HeOuJ mice (Jackson Laboratories), aged 5 to 6 weeks with body weights of 23.2 g, were used. Animals had jugular cannulas installed by Jackson Laboratories prior to shipment, and were individually numbered using an ear punch and individually housed. Animals were acclimatized prior to study commencement. During this period of at least 2 days, the animals were observed daily in order to reject animals that presented in poor condition.

4.2 Housing

The study was performed in animal rooms as described above in section 4.2 of Example I.

4.3 Diet

Animals were fed with Labdiet® 5061 sterile irradiated rodent chow and water was provided ad libitum.

4.4 Animal Randomization and Allocations

Mice were randomly and prospectively divided into three (3) treatment groups prior to irradiation. Each animal was identified by an ear punch corresponding to an individual number. A cage card was used to identify each cage or label marked with the study number, treatment group number, and animal numbers.

4.5 Radiation

Machine calibration was checked within two weeks of the onset of this study. A single dose of radiation (30 Gy/dose) was administered to all animals in groups 1 and 2 on day 0. Radiation was generated with a 160 kilovolt potential (15-ma) source at a focal distance of 50 cm, hardened with a 0.35 mm Cu filtration system. Irradiation was done at a rate of 121.5 cGy/minute. Animals were anesthetized prior to radiation, and placed under lead shielding such that only the snout is exposed

4.6 Tissue Collection and Analysis

4.6.1 Histology

Histological samples were fixed in 10% formaldehyde in saline and processed for paraffin histology using standard techniques. Slides were stained with hematoxylin and eosin (H&E).

4.6.2 Cytokine ELISA

Enzyme linked immunosorbent assays (ELISAs) were performed for cytokines TNF-$\alpha$ and IL-6 using kits purchased from R and D systems. Determination of serum amyloid A was performed using an ELISA kit from Biosource International. These kits were used in accordance with the manufacturer's instructions. All determinations were made in duplicate on serum samples stored at $-80°$ C. Samples were run in duplicate in all three assays, and if insufficient serum had been collected to run IL-6, SAA, and TNF-$\alpha$ assays, samples were diluted 1:4. All assays were performed using 50 μL of sample per well.

4.7 Assessment of Results

Statistical differences between treatment groups were determined using One Way ANOVA. Body weights are evaluated for differences between the treatment groups.

5. Results and Discussion

5.1 Survival

A total of 108 cannulated animals were used in this study. Due to the limited availability of the C3H/HeOuJ mice, these animals were processed in 3 groups over a period of 6 weeks. 57 of these mice survived until day 10. Of the 51 mice that did not survive until day 10, 21 died or were euthanized on day 0, 11 due to anesthesia and radiation related issues, and 10 due to problems with the cannula (died after initial injection due to presumed clot, cannula not patent, or cannula pulled out). Of the remaining 30 animals that died or were enthanized during the study, 2 died on day 1, 5 on day 2, 4 on day 3, 7 on day 4, 3 each on days 5 and 6, 1 each on days 7 and 8, and 2 each on days 9 and 10. The distribution of deaths by group was relatively equal. Nine (9) deaths were observed in each of the un-irradiated control group and the vehicle control group. Seven (7) deaths were observed in each of the groups treated with eritoran 10 mg/kg from days 0-10 or days 0-3. Nine deaths were observed in the group treated with eritoran 10 mg/kg, from day 3 until day 6, and 10 deaths were observed in the group treated with eritoran 10 mg/kg, from day 6 until day 9.

5.2 Weights (FIGS. 17, 18, 19, and 20)

Figure 17:
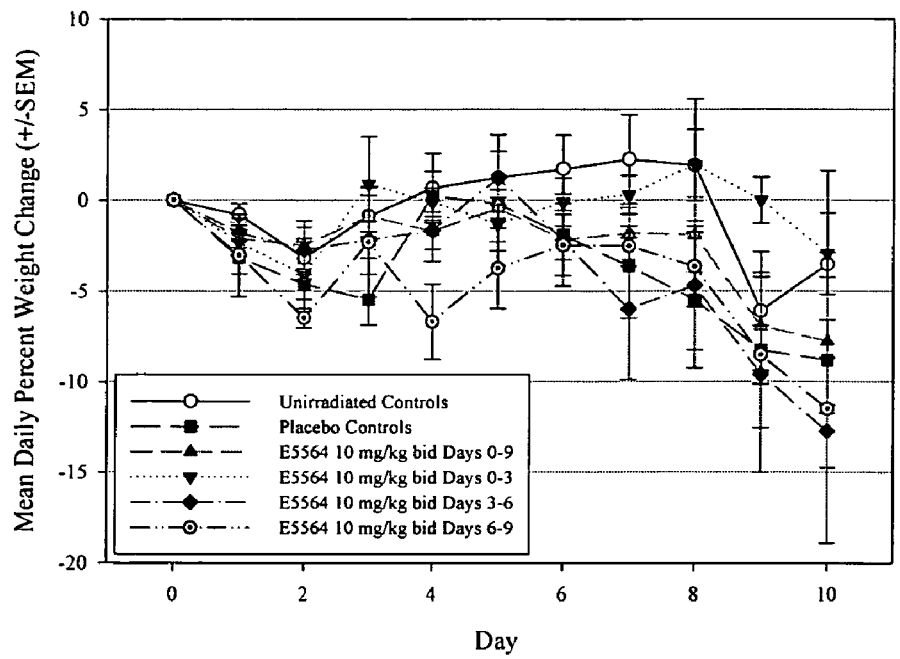
FIG. 17 is a graph showing the percent weight change of animals treated with eritoran (E5564) under the indicated regimens, as well as un-irradiated and placebo controls. Animals were weighed daily, the percent weight change from day 0 was calculated, and group means and standard errors of the mean (SEM) calculated for each day.
Figure 18:
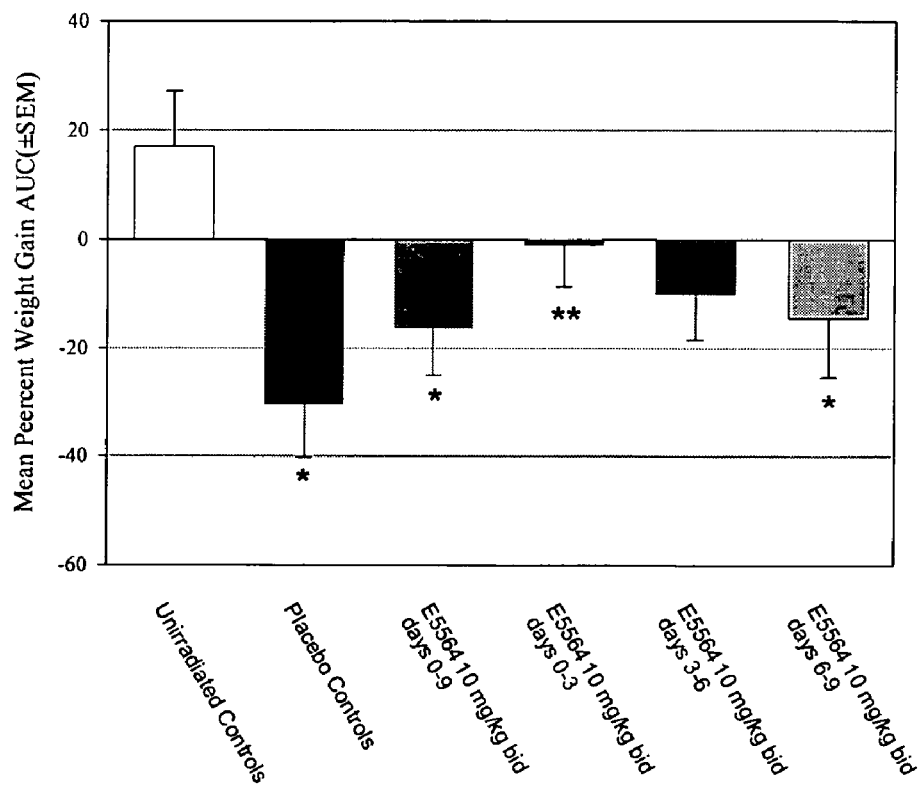
FIG. 18 is a graph showing the area under the curve (AUC) calculated for the percent weight change exhibited by each animal in the study. This calculation was made using the trapezoidal rule transformation. Group means were calculated and are shown with error bars representing SEM for each group. A single asterisk signifies a statistically significant difference between a group receiving radiation and the un-irradiated controls, two asterisks indicate a statistically significant difference between the group treated with eritoran on days 0-3, and the placebo controls (irradiated) (P=0.030).
Figure 19:
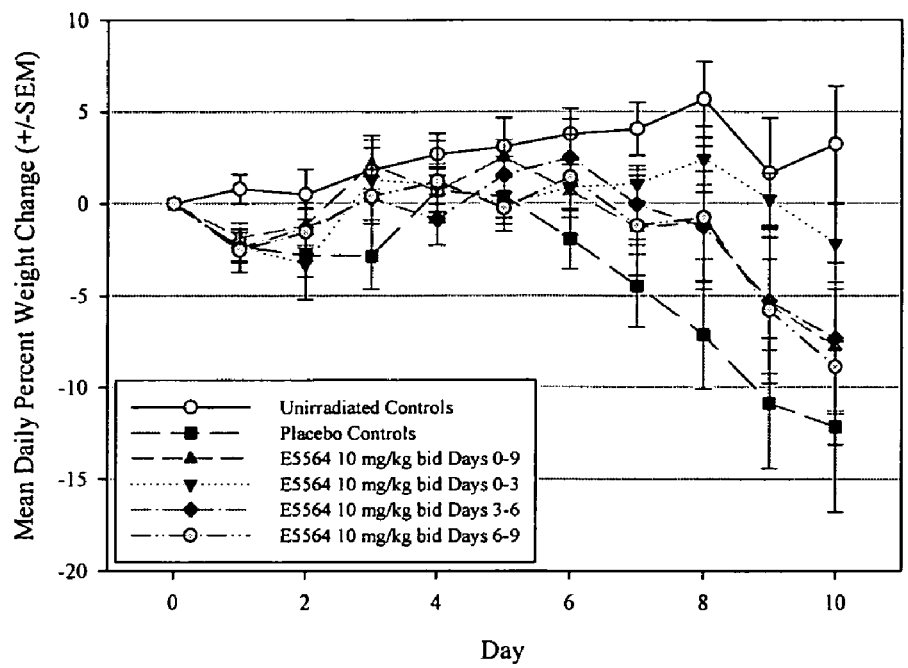
FIG. 19 is a graph showing the percent weight change of animals treated according to the regimens indicated in the figure. Data are shown for animals surviving until the end of the study only. Animals were weighed daily, the percent weight change from day 0 was calculated, and group means and standard errors of the mean (SEM) calculated for each day.
Figure 20:
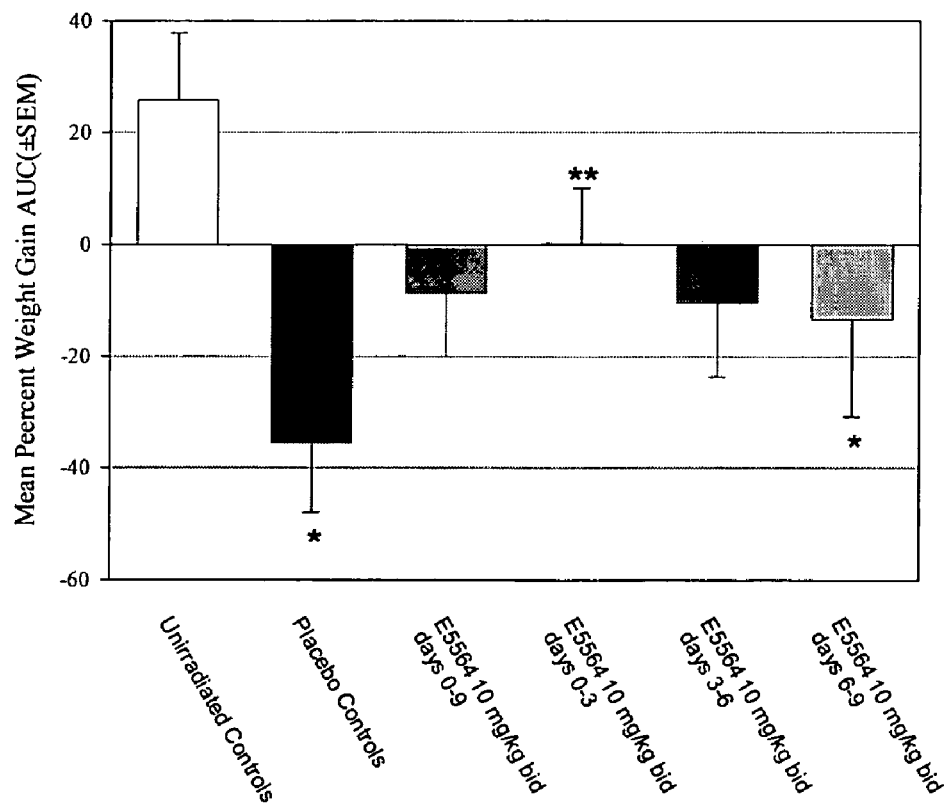
FIG. 20 is a graph showing the area under the curve (AUC) calculated for the percent weight change exhibited by each animal treated, according to the regimens noted in the graph. This calculation was made using the trapezoidal rule transformation. Group means were calculated and are shown with error bars representing SEM for each group. A single asterisk signifies a statistically significant difference between a group receiving radiation and the un-irradiated controls, two asterisks indicate a statistically significant difference between the group treated with eritoran on days 0-3, and the placebo controls (irradiated) (P=0.041).

The mean percentage weight gain for each group for each day of the study is shown in FIG. 17. The un-irradiated control group gained and average of 3.2% during the study, as compared with a mean loss of 12.1% in the placebo group. In the groups receiving eritoran at 10 mg/kg, a mean weight loss of 7.8% was seen in the group treated on days 0-10 as compared with a net loss of 2.2% in the group treated on days 0 to 3, a net loss of 7.3% in the group treated on days 3 to 6, and a net loss of 8.9% for the group treated on days 6 to 9. To determine whether the differences observed in weight change were significant, a One-Way ANOVA on the mean Area Under the Curve (AUC) data was performed. The results of this analysis are shown in FIG. 18. Three groups receiving radiation were significantly different from the un-irradiated controls, the placebo group (P<0.001), the group treated with eritoran from day 0 until day 10 (P=0.014), and the group treated with eritoran from day 6 to day 9 (P=0.025). The groups treated with eritoran from day 0 until day 3 or from day 3 to day 6 were not significantly different than the un-irradiated controls. However, the group treated with eritoran from day 0 until day 3 had significantly less weight loss than the placebo controls (P=0.030). The weight data was reanalyzed with the data from all animals dying during the study removed. The results of this analysis are shown in FIGS. 19 and 20. There was little change in the results of the One-Way ANOVA analysis, except that the group treated with eritoran from day 0 until day 9 was not significantly different from the un-irradiated controls in this analysis.

5.3 Tongue Histology

Each tongue was processed for routine hematoxylin and eosin histology and slides were reviewed in a blinded manner. A total of 57 samples were evaluated, and of these, 9 were in the un-irradiated control group, 9 were in the placebo group, 11 were in the group treated with eritoran at 10 mg/kg from day 0 to day 9, 11 were in the group treated with eritoran at 10 mg/kg from day 0 to day 3, 9 were in the group treated with eritoran at 10 mg/kg from day 3 to day 6, and 9 were in the group treated with eritoran at 10 mg/kg from day 6 to day 9. Three sections from each sample were evaluated for the following parameters: epitheial score, connective tissue score, inflammation score, mitoses per 10 high power fields (hpf), percent ulceration, number of inflammatory cells per 10 hpf (percent neutrophils, lymphocytes, and monocytes/macrophage), the number of small, medium, and large blood vessels per 10 hpf, and the number of mast cells per 10 hpf.

5.3.1 Epithelial Score

Figure 21:
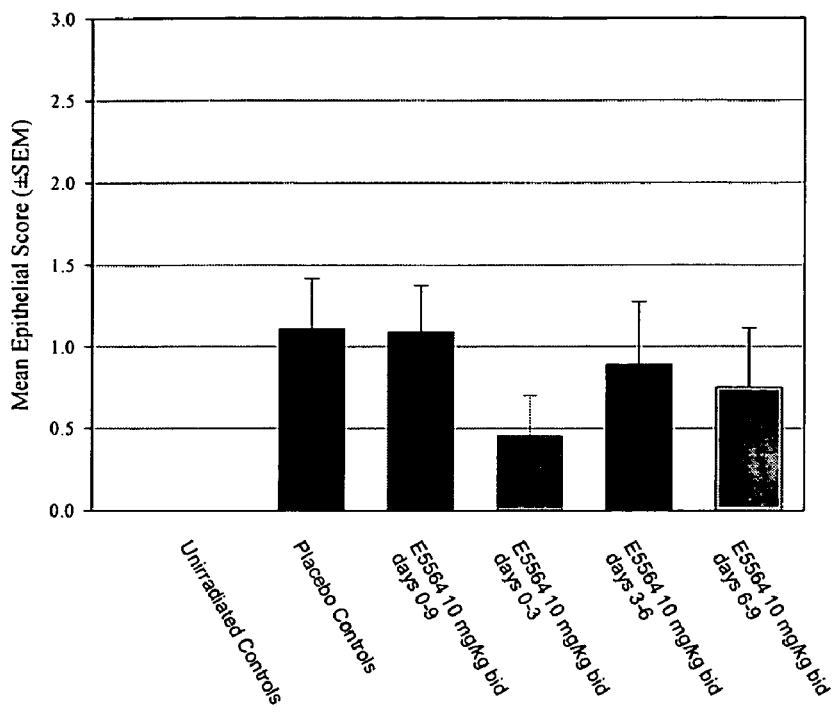
FIG. 21 is a graph showing mean epithelial scores and standard errors of the mean for each of the indicated groups.

Epithelial histology was scored on a 4 point 0-3 scale as outlined in section 4.7.1. These scores are shown in FIG. 21. The un-irradiated animals all had scores of 0. The placebo control group had a mean score of 1.1, as did the group treated with eritoran at 10 mg/kg from day 0 to day 9. The group treated with eritoran at 10 mg/kg from day 0 to day 3 had a mean score of 0.45. The group treated with eritoran at 10 mg/kg from day 3 to day 6 had a mean score of 0.89. The group treated with eritoran at 10 mg/kg from day 6 to day 9 had a mean score of 0.75.

5.3.2 Connective Tissue Score

Figure 22:
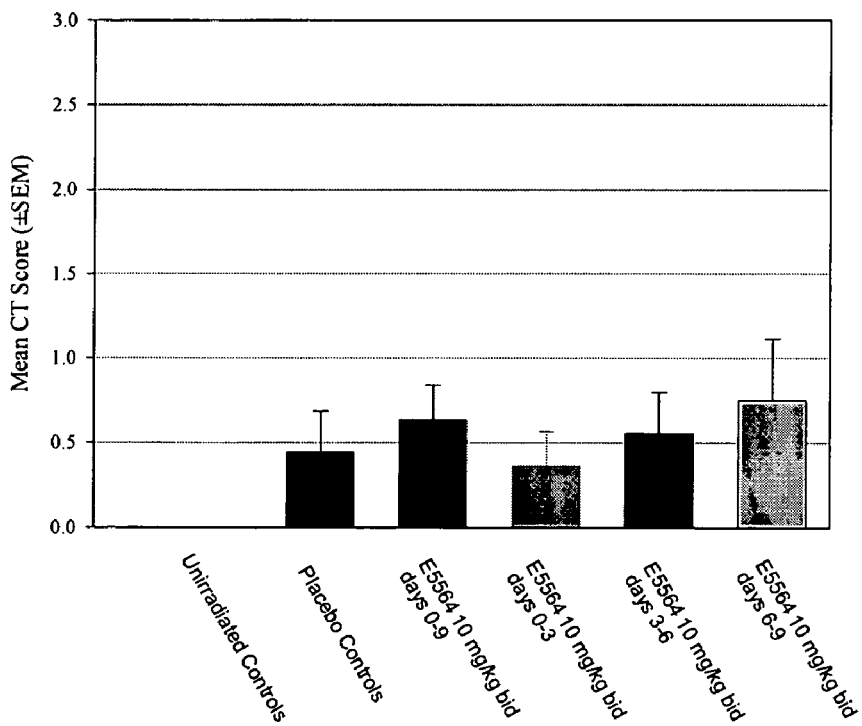
FIG. 22 is a graph showing mean connective tissue scores and standard errors of the mean for each of the indicated groups.

Connective histology was scored on a 4 point 0-3 scale as outlined in section 4.7.1. These scores are shown in FIG. 22. The un-irradiated animals all had scores of 0. The placebo control group had a mean score of 0.4, the group treated with eritoran at 10 mg/kg from day 0 to day 9 had a mean score of 0.6. The group treated with eritoran at 10 mg/kg from day 0 to day 3 had a mean score of 0.4. The group treated with eritoran at 10 mg/kg from day 3 to day 6 had a mean score of 0.6. The group treated with eritoran at 10 mg/kg from day 6 to day 9 had a mean score of 0.8.

5.3.3 Inflammation Score

Figure 23:
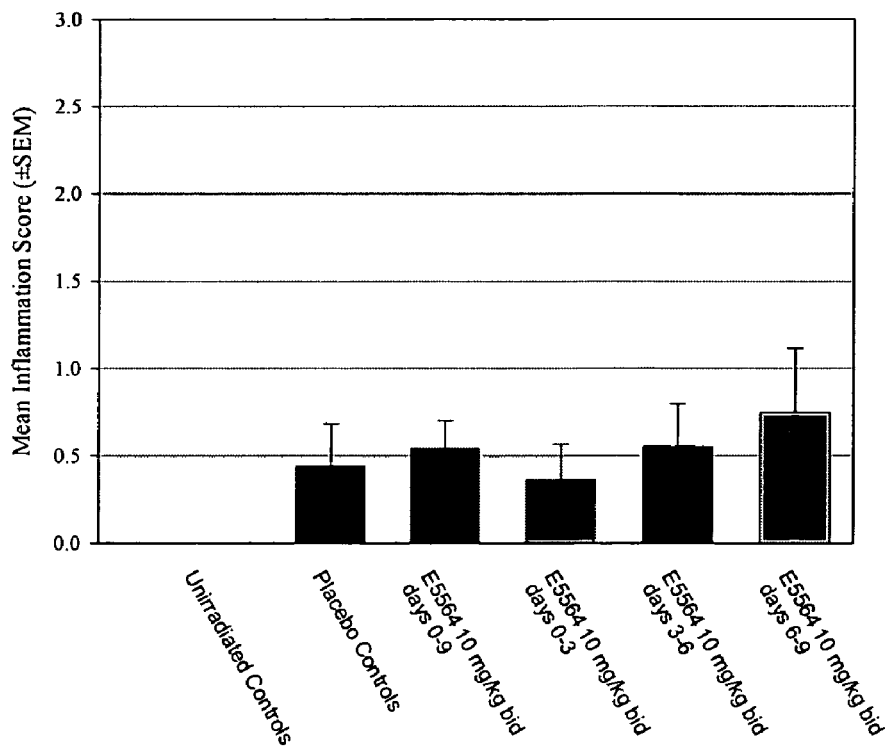
FIG. 23 is a graph showing mean inflammation scores and standard errors of the mean for each of the indicated groups.

Inflammation was scored on a 4 point 0-3 scale as outlined in section 4.7.1. These scores are shown in FIG. 23. The un-irradiated animals all had scores of 0. The placebo control group had a mean score of 0.4, the group treated with eritoran at 10 mg/kg from day 0 to day 9 had a mean score of 0.5. The group treated with eritoran at 10 mg/kg from day 0 to day 3 had a mean score of 0.4. The group treated with eritoran at 10 mg/kg from day 3 to day 6 had a mean score of 0.6. The group treated with eritoran at 10 mg/kg from day 6 to day 9 had a mean score of 0.8.

5.3.4 Number of Mitoses

Figure 24:
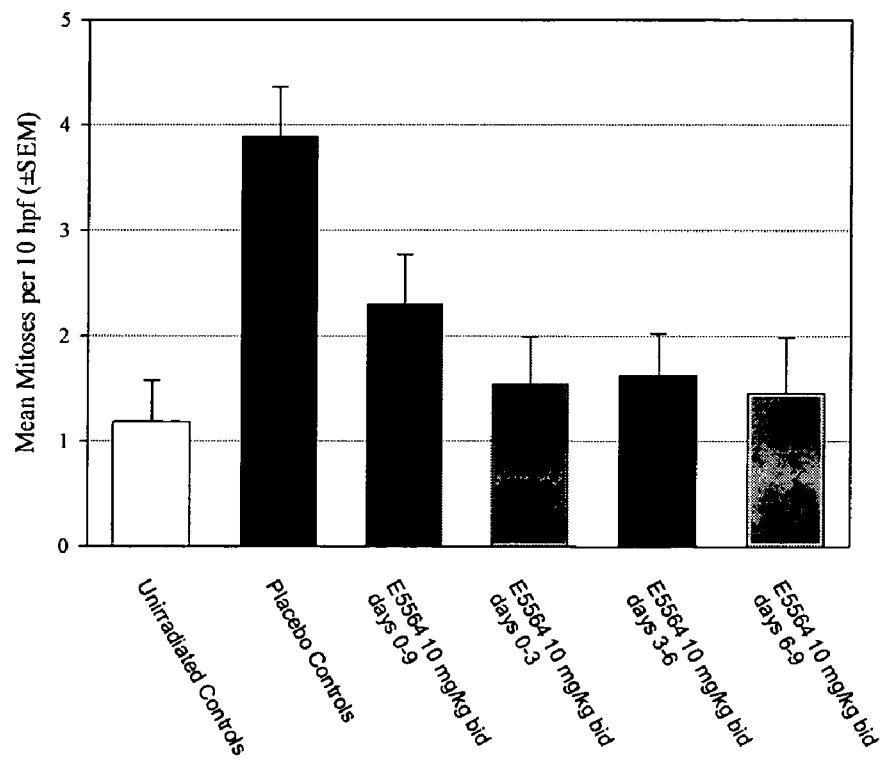
FIG. 24 is a graph showing mean number of mitoses per 10 hpf and standard errors of the means for each of the indicated groups.

The number of mitoses was counted in 10 high power fields (hpf). These data are shown in FIG. 24. The un-irradiated animals had an average of 1.2 mitoses per 10 hpf. The placebo control group had an average of 3.9 mitoses per 10 hpf. The group treated with eritoran at 10 mg/kg from day 0 to day 9 had an average of 2.3 mitoses per 10 hpf. The group treated with eritoran at 10 mg/kg from day 0 to day 3 had an average of 1.5 mitoses per 10 hpf. The group treated with eritoran at 10 mg/kg from day 3 to day 6 had an average of 1.6 mitoses per 10 hpf. The group treated with eritoran at 10 mg/kg from day 6 to day 9 had an average of 1.5 mitoses per 10 hpf.

5.3.5 Percent Ulceration

Figure 25:
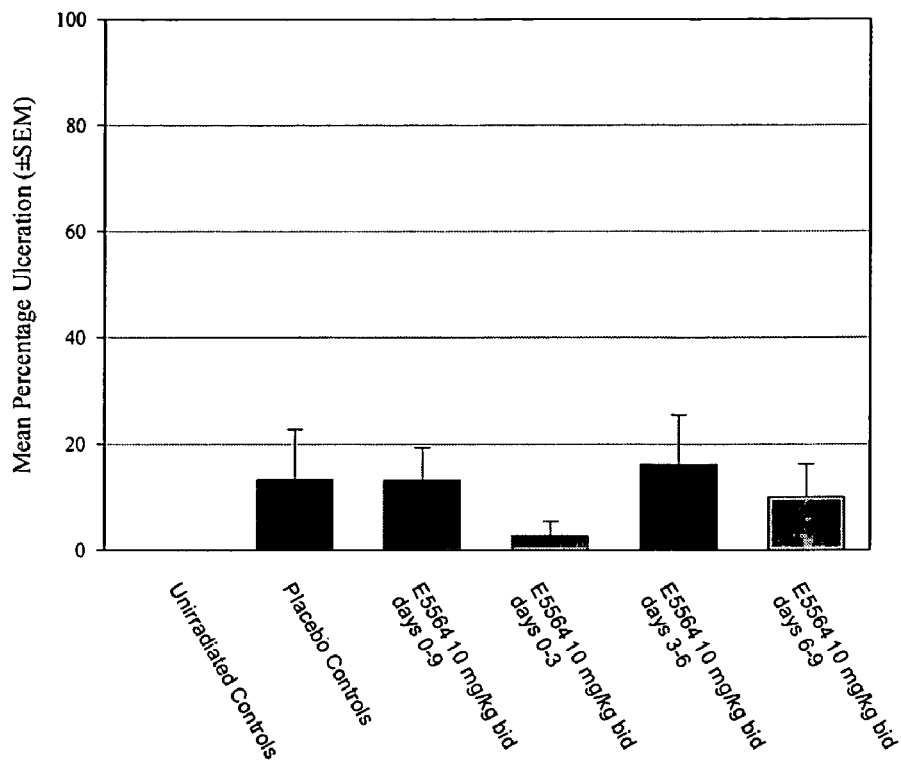
FIG. 25 is a graph showing the mean percent ulceration and standard error of the mean for each of the indicated groups.

The percentage ulceration was estimated for each sample. These data are shown in FIG. 25. The un-irradiated animals had no ulceration. The placebo control group had mean ulceration of 13.3%. The group treated with eritoran at 10 mg/kg from day 0 to day 9 had mean ulceration of 13.2%. The group treated with eritoran at 10 mg/kg from day 0 to day 3 had mean ulceration of 2.7%. The group treated with eritoran at 10 mg/kg from day 3 to day 6 had mean ulceration of 16.7%. The group treated with eritoran at 10 mg/kg from day 6 to day 9 had mean ulceration of 10.0%.

5.3.6 Inflammatory Cell Infiltrates

Figure 26:
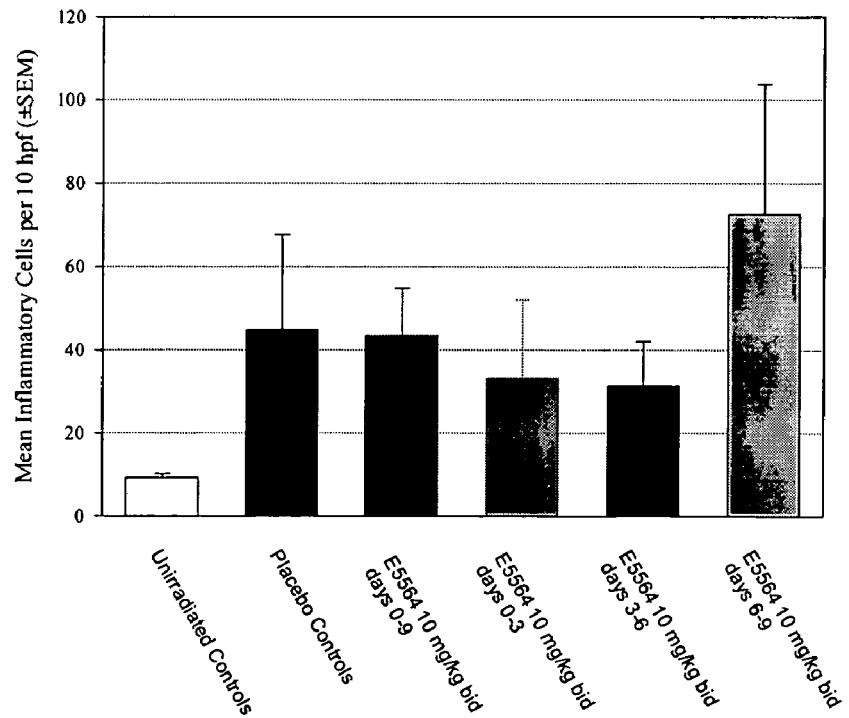
FIG. 26 is a graph showing the mean number of inflammatory cells per 10 hpf and standard errors of the means for each of the indicated groups.
Figure 27:
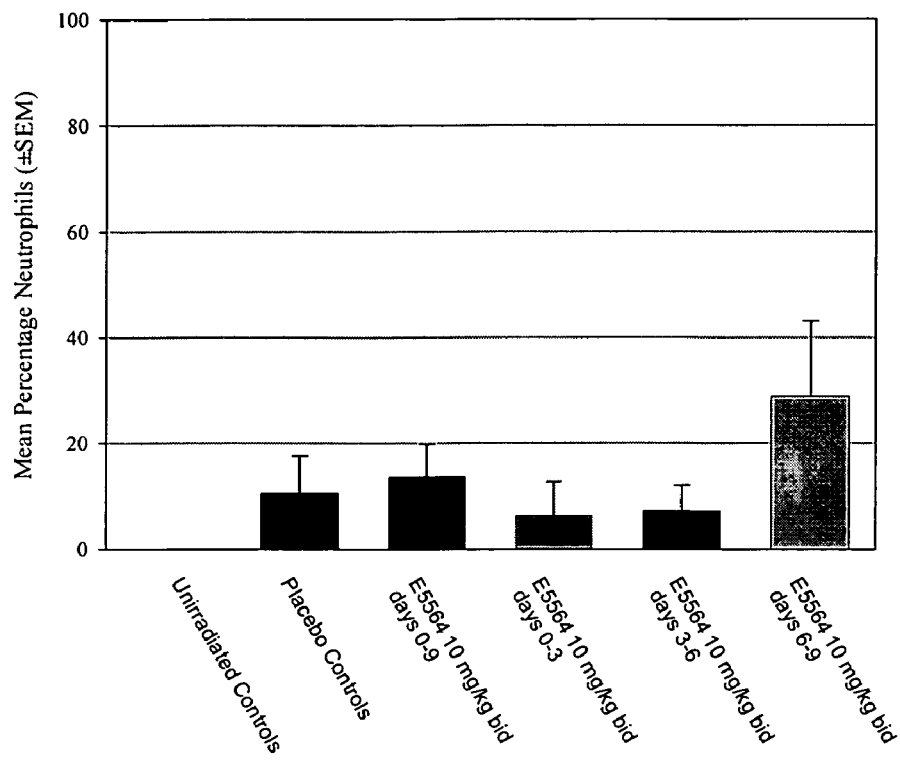
FIG. 27 is a graph showing the percentage of the infiltrating inflammatory cells that were neutrophils for each sample and the mean and standard deviation for each of the indicated groups.
Figure 28:
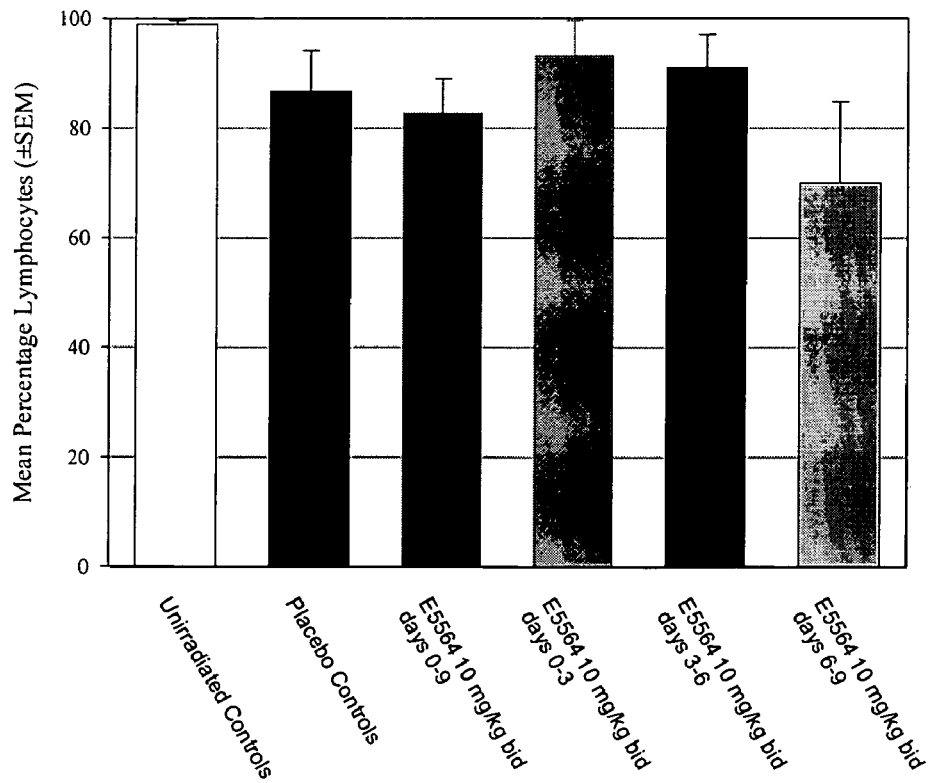
FIG. 28 is a graph showing the percentage of the infiltrating inflammatory cells that were lymphocytes for each sample and the mean and standard deviation for each of the indicated groups.
Figure 29:
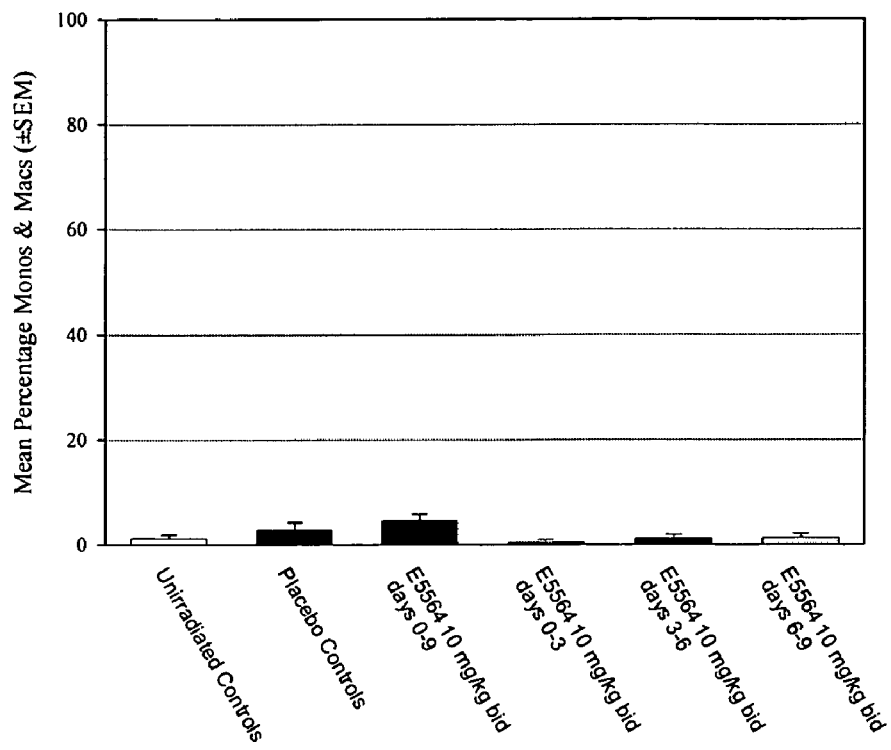
FIG. 29 is a graph showing the percentage of the infiltrating inflammatory cells that were monocytes or macrophage for each sample and the mean and standard deviation for each of the indicated groups.

The inflammatory cell infiltrate present in each sample was enumerated by counting the total number of inflammatory cells per 10 hpf, and evaluated for cell type by estimating the percentage of cells within the infiltrate that were neutrophils, lymphocytes, or monocytes/macrophage. The numbers of inflammatory cell data are shown in FIG. 26, the percent neutrophils in FIG. 27, the percent lymphocytes in FIG. 28, and the percent monocytes/macrophage in FIG. 29. The un-irradiated animals had an average of 9.3 cells per 10 hpf, with an average composition of 98.9% lymphocytes and 1.1% monocytes/macrophage, with no neutrophils seen. The placebo control group had an average of 44.9 cells per 10 hpf, with an average composition of 10.6% neutrophils, 86.7% lymphocytes, and 2.8% monocytes/macrophage. The group treated with eritoran at 10 mg/kg from day 0 to day 9 had an average of 43.6 cells per 10 hpf, with an average composition of 13.6% neutrophils, 82.7% lymphocytes, and 4.5% monocytes/macrophage. The group treated with eritoran at 10 mg/kg from day 0 to day 3 had an average of 33.3 cells per 10 hpf, with an average composition of 6.4% neutrophils, 93.2% lymphocytes, and 0.5% monocytes/macrophage. The group treated with eritoran at 10 mg/kg from day 3 to day 6 had an average of 31.5 cells per 10 hpf, with an average composition of 7.2% neutrophils, 91.1% lymphocytes, and 1.1% monocytes/macrophage. The group treated with eritoran at 10 mg/kg from day 6 to day 9 had an average of 52.1 cells per 10 hpf, with an average composition of 8% neutrophils, 91.0% lymphocytes, and 1.0% monocytes/macrophage.

5.3.7 Blood Vessels

Figure 30:
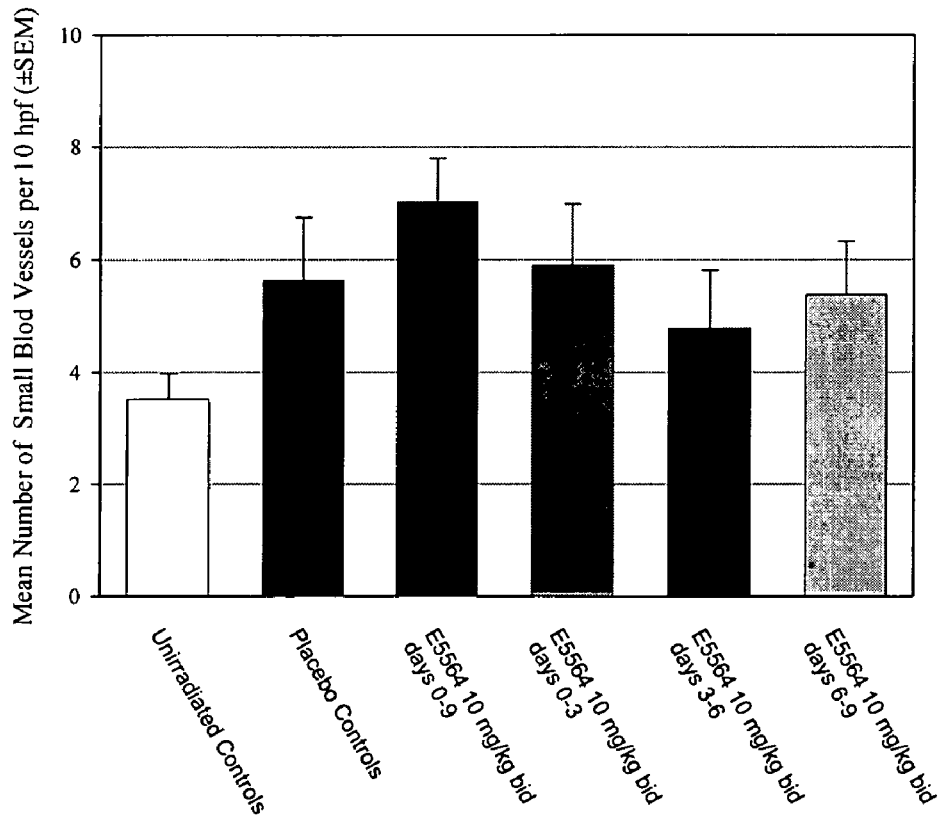
FIG. 30 is a graph showing the number of small blood vessels per 10 hpf and the mean and standard errors of the means for each of the indicated groups.
Figure 31:
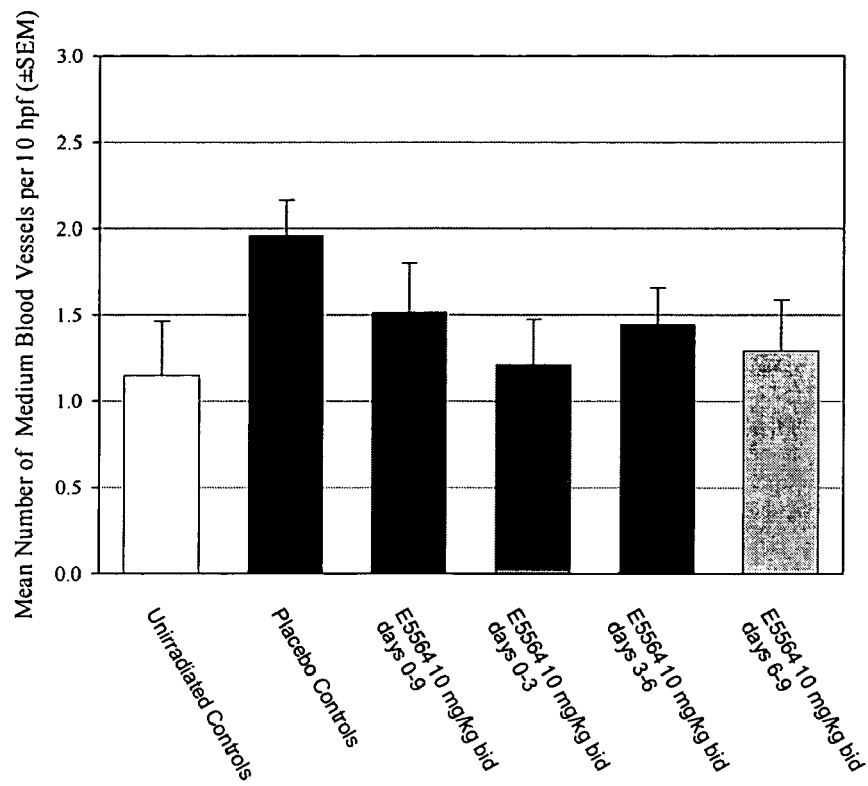
FIG. 31 is a graph showing the number of medium blood vessels per 10 hpf and the means and standard errors of the means for each of the indicated groups.
Figure 32:
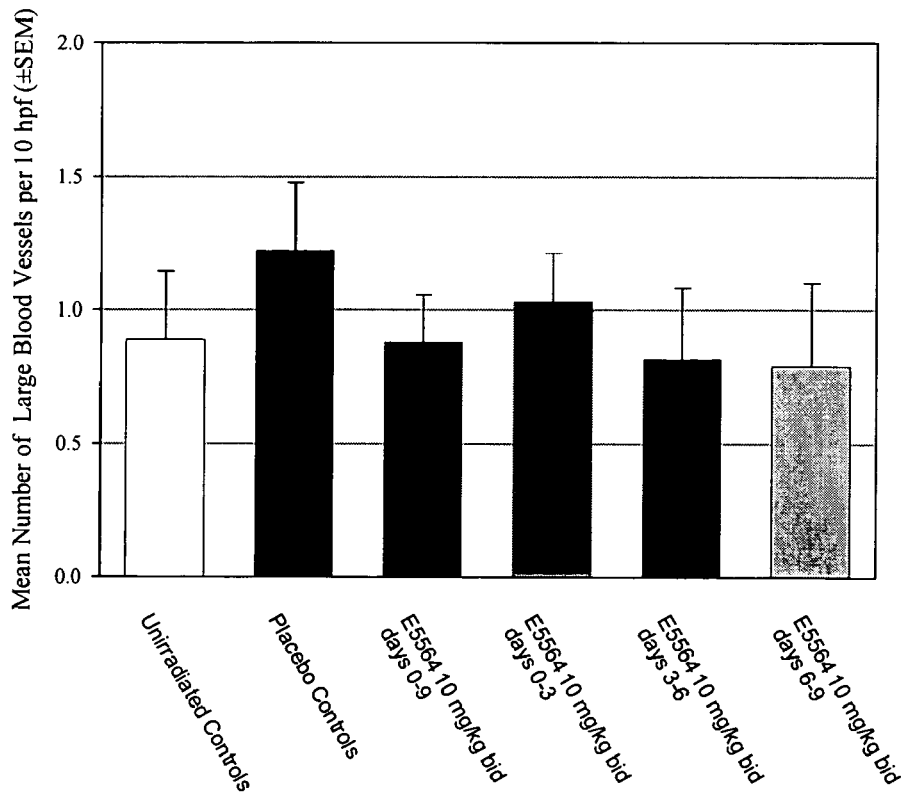
FIG. 32 is a graph showing the number of large blood vessels per 10 hpf and the means and standard errors of the means for each of the indicated groups.

The number of blood vessels present in each sample was quantified by counting the total number of blood vessels in 10 hpf, and evaluated for vessel size by counting the number of small, medium, and large vessels in this sample. These data are shown in FIGS. 30-32. The un-irradiated animals had an average of 5.6 blood vessels per 10 hpf, with an average composition of 63.3% small, 20.7% medium, and 16.0% large vessels seen. The placebo control group had an average of 8.8 blood vessels per 10 hpf, with an average composition of 63.9% small, 22.3% medium, and 13.9% large vessels. The group treated with eritoran at 10 mg/kg from day 0 to day 9 had an average of 9.4 blood vessels per 10 hpf, with an average composition of 74.6% small, 16.1% medium, and 9.3% large vessels seen. The group treated with eritoran at 10 mg/kg from day 0 to day 3 had an average of 8.2 blood vessels per 10 hpf, with an average composition of 72.5% small, 14.9% medium, and 12.6% large vessels. The group treated with eritoran at 10 mg/kg from day 3 to day 6 had an average of 7.0 blood vessels per 10 hpf, with an average composition of 67.9% small, 20.5% medium, and 11.6% large vessels. The group treated with eritoran at 10 mg/kg from day 6 to day 9 had an average of 7.5 blood vessels per 10 hpf, with an average composition of 72.1% small, 17.3% medium, and 10.6% large vessels.

5.3.8. Mast Cells

Figure 33:
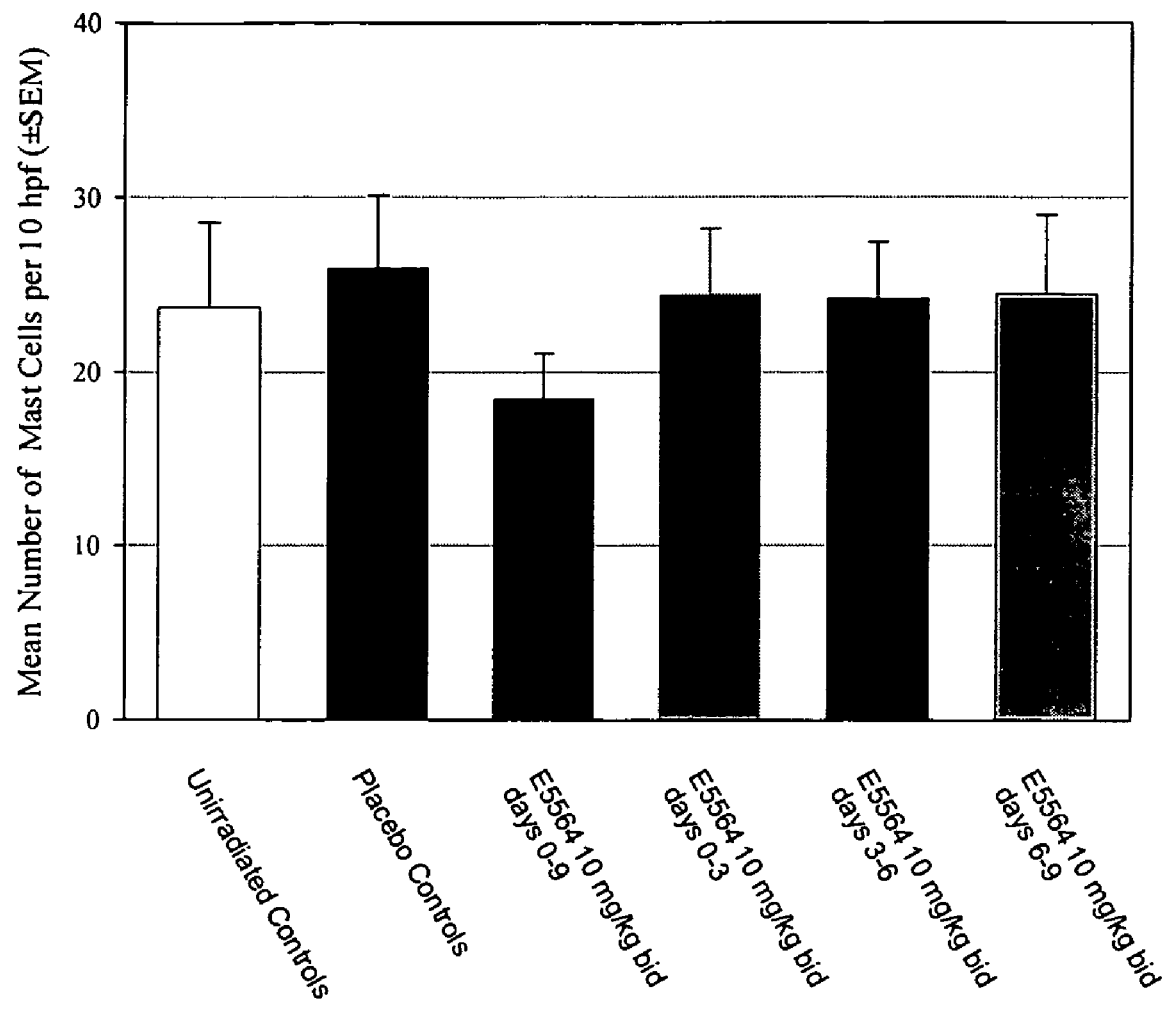
FIG. 33 is a graph showing the number of mast cells per 10 hpf and the means and standard errors of the means for each of the indicated groups.

The number of mast cells present in each sample was determined by counting the number cells per 10 hpf. These data are shown in FIG. 33. The un-irradiated animals had 23.7 mast cells per 10 hpf. The placebo control group had 26 mast cells per 10 hpf. The group treated with eritoran at 10 mg/kg from day 0 to day 9 had 18.4 mast cells per 10 hpf. The group treated with eritoran at 10 mg/kg from day 0 to day 3 had 24.4 mast cells per 10 hpf. The group treated with eritoran at 10 mg/kg from day 3 to day 6 had 24.2 mast cells per 10 hpf. The group treated with eritoran at 10 mg/kg from day 6 to day 9 had 24.5 mast cells per 10 hpf.

5.4 Serum Cytokine Levels

Serum levels of TNF-$\alpha$, IL-6, and SAA were measured using commercially available ELISA kits.

5.4.1 Serum TNF-$\alpha$ Levels

Figure 34:
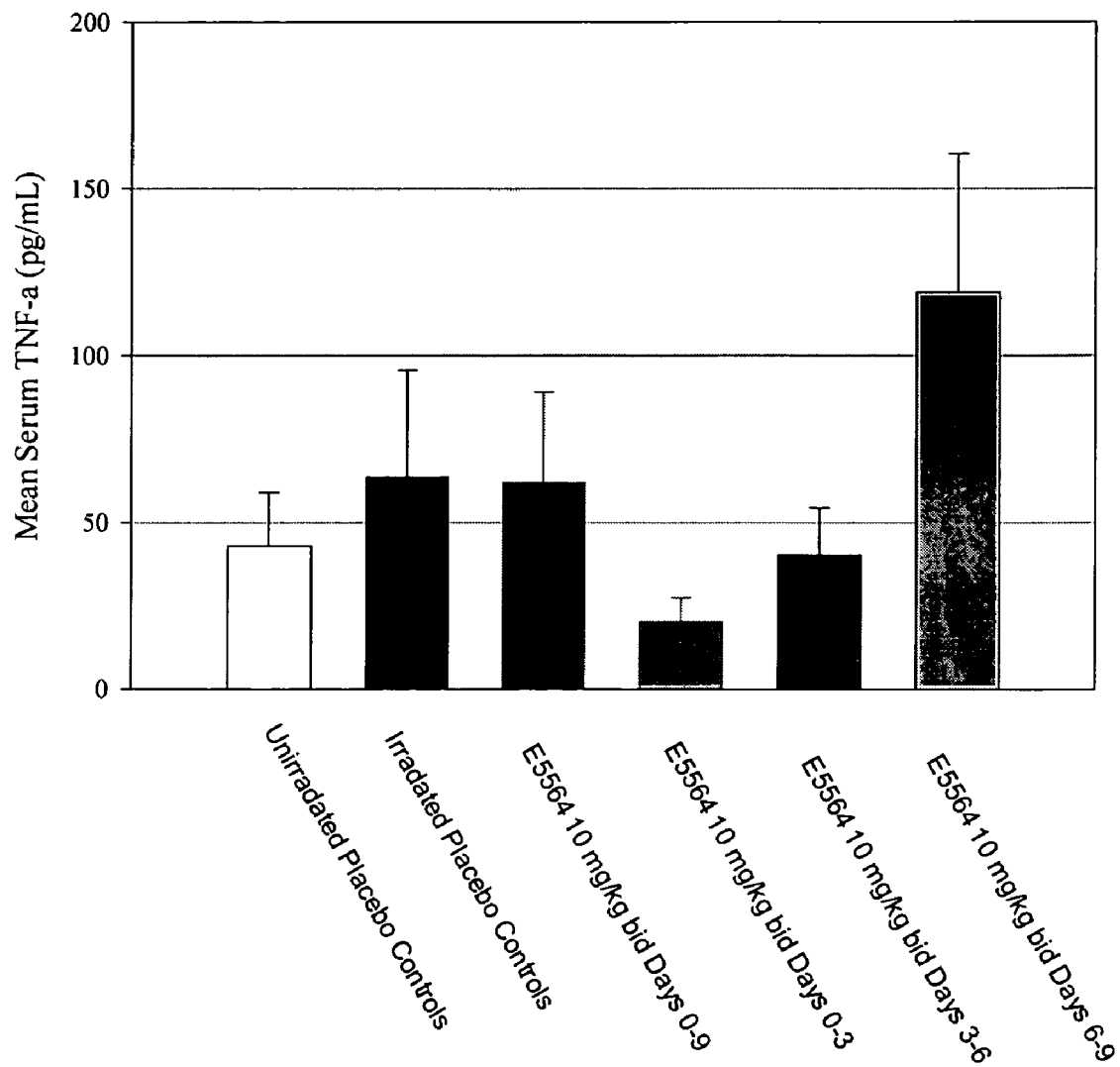
FIG. 34 is a graph showing serum TNF-α levels measured using an ELISA assay and the mean and standard error of the mean for each of the indicated groups.

The un-irradiated animals had serum TNF-$\alpha$ levels of 43.0 pg/mL. The placebo control group had mean serum TNF-$\alpha$ levels of 63.8 pg/mL. The group treated with eritoran at 10 mg/kg from day 0 to day 9 had mean serum TNF-$\alpha$ levels of 62.0 pg/mL. The group treated with eritoran at 10 mg/kg from day 0 to day 3 had mean serum TNF-$\alpha$ levels of 20.3 pg/mL. The group treated with eritoran at 10 mg/kg from day 3 to day 6 had mean serum TNF-$\alpha$ levels of 40.2 pg/mL. The group treated with eritoran at 10 mg/kg from day 6 to day 9 had mean serum TNF-$\alpha$ levels of 119.1 pg/mL. These data are shown in FIG. 34.

5.4.2 Serum IL-6 Levels

Figure 35:
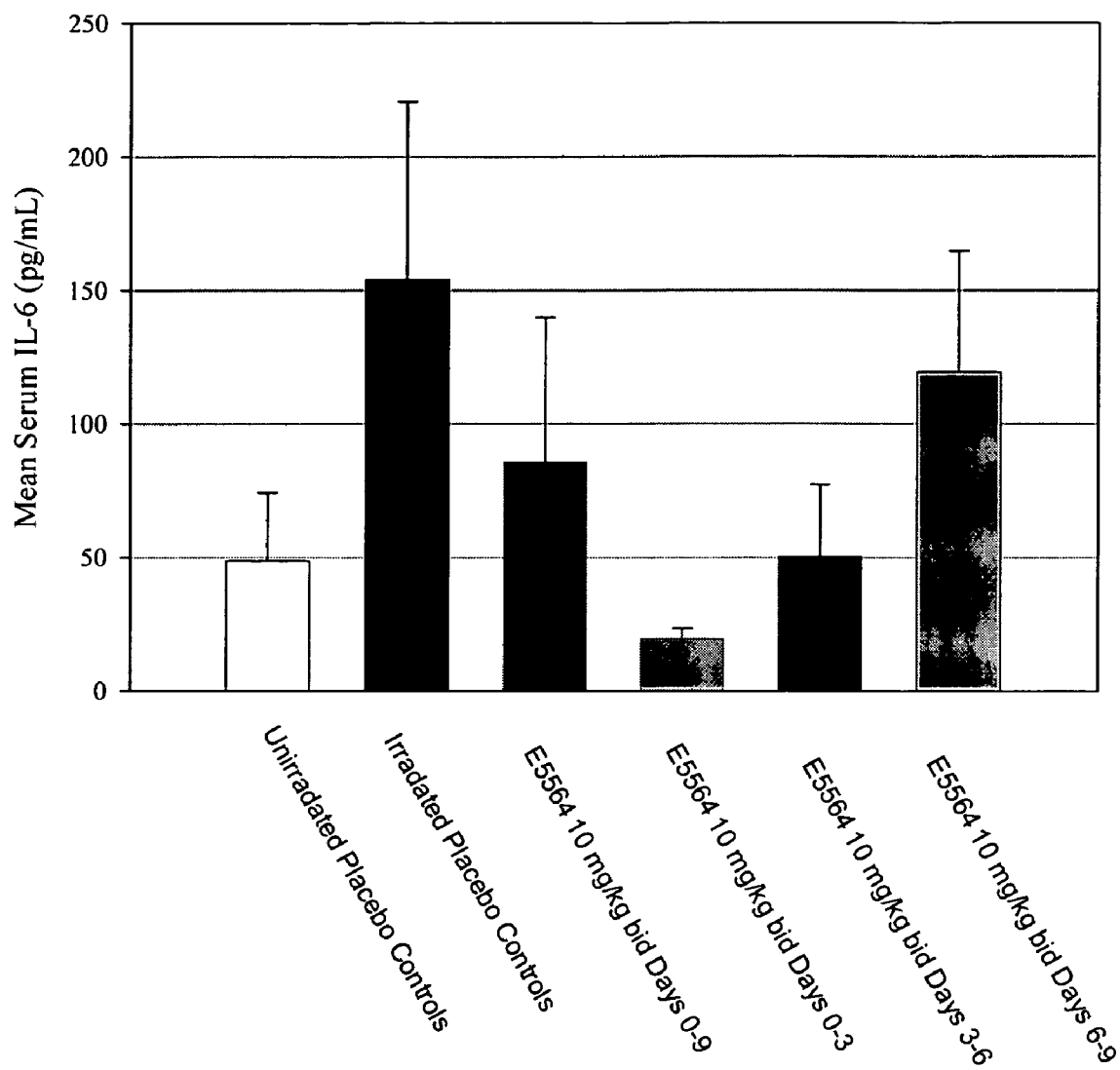
FIG. 35 is a graph showing serum IL-6 levels measured using an ELISA assay and the mean and standard error of the mean for each of the indicated groups.

The un-irradiated animals had serum IL-6 levels of 48.7 pg/mL. The placebo control group had mean serum IL-6 levels of 154.2 pg/mL. The group treated with eritoran at 10 mg/kg from day 0 to day 9 had mean serum IL-6 levels of 85.6 pg/mL. The group treated with eritoran at 10 mg/kg from day 0 to day 3 had mean serum IL-6 levels of 19.7 pg/mL. The group treated with eritoran at 10 mg/kg from day 3 to day 6 had mean serum IL-6 levels of 50.4 pg/mL. The group treated with eritoran at 10 mg/kg from day 6 to day 9 had mean serum IL-6 levels of 119.3 pg/mL. These data are shown in FIG. 35.

5.4.3 Serum SAA Levels

Figure 36:
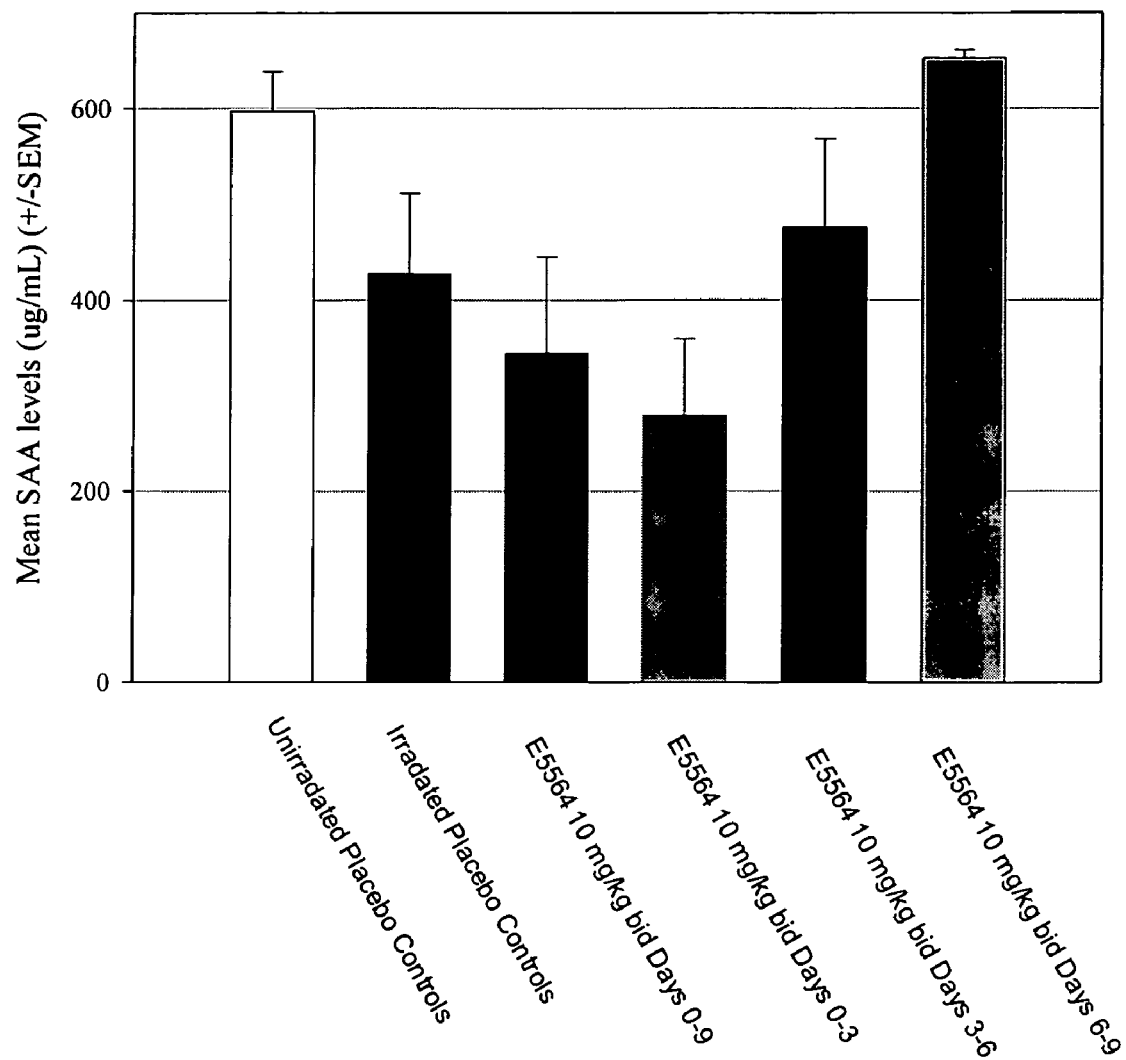
FIG. 36 is a graph showing serum SAA levels measured using an ELISA assay and the mean and standard error of the mean for each of the indicated groups.

The un-irradiated animals had serum SAA levels of 597 μg/mL. The placebo control group had mean serum SAA levels of 427 μg/mL. The group treated with eritoran at 10 mg/kg from day 0 to day 9 had mean serum SAA levels of 344 μg/mL. The group treated with eritoran at 10 mg/kg from day 0 to day 3 had mean serum SAA levels of 279 μg/mL. The group treated with eritoran at 10 mg/kg from day 3 to day 6 had mean serum SAA levels of 475 μg/mL. The group treated with eritoran at 10 mg/kg from day 6 to day 9 had mean serum SAA levels of 652 μg/mL. These data are shown in FIG. 36.

6. Conclusions

1. There was no evidence of toxicity with eritoran in the mortality or weight loss data from this study. As with previous studies, mortality was high, but evenly distributed across groups.

2. Mice treated with eritoran on days 0-3 showed a significant improvement in weight loss relative to the placebo treated control group.

3. The levels of oral mucositis observed in the placebo treated control mice were lower than anticipated, and made it difficult to assess the impact of eritoran on the levels of oral mucositis seen.

4. Possibly due to the relatively low levels of mucositis seen in the placebo control group, little effect was seen in the group treated with eritoran at 10 mg/kg from day 0 to day 9, in contrast to previous observations of efficacy with this treatment protocol.

5. Among the groups receiving radiation, the group treated with eritoran on days 0-3 had the lowest epithelial score, connective tissue score, and percent ulceration, indicating that it had suffered less damage than other groups. This group also had the lowest inflammation score and was second lowest in the number of inflammatory cells and mitoses.

6. Among the groups receiving radiation, the group treated with eritoran on days 0-3 had the lowest serum levels of TNF-α, IL-6, and SAA, showing the efficacy of this regimen in reducing inflammatory responses.

What is claimed is:

1. A method of reducing the severity of mucositis in a patient the method comprising the step of administering to the patient, by intravenous infusion, a composition comprising a compound that blocks activation of toll-like receptor 4, wherein the compound is a lipid A analog of the structure:

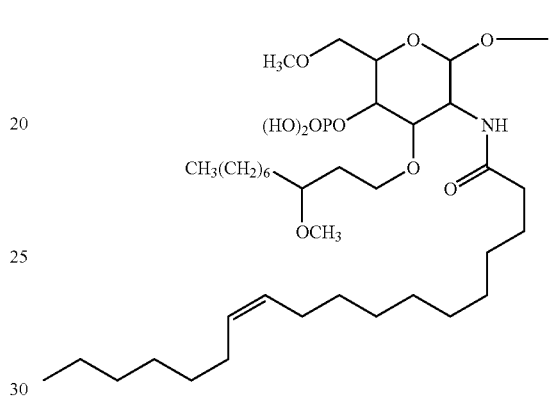

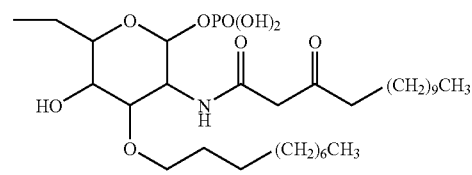

or a pharmaceutically acceptable salt or phosphate ester thereof.

2. The method of claim 1, wherein the lipid A analog is of the structure:

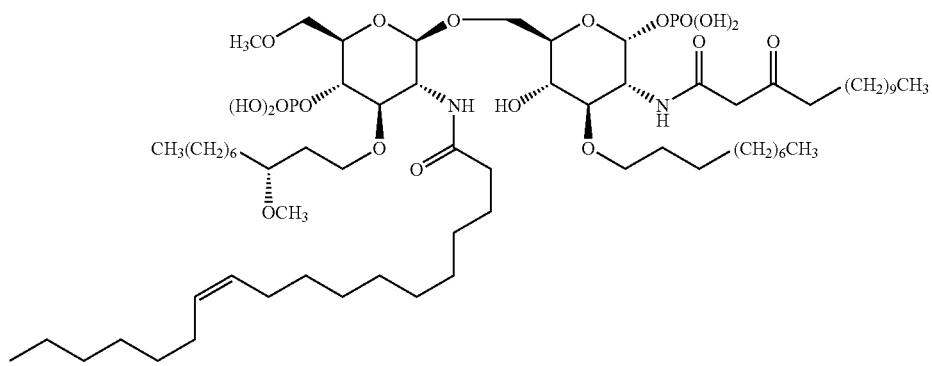

or a pharmaceutically acceptable salt or phosphate ester thereof.

3. The method of claim 1, wherein the mucositis is oral mucositis.

4. The method of claim 1, wherein the mucositis is of the gastrointestinal tract.

5. The method of claim 1, wherein the patient has mucositis.

6. The method of claim 1, wherein the patient does not have, but is at risk of developing, mucositis.

7. The method of claim 6, wherein development of mucositis is inhibited in the patient by administration of the composition.

8. The method of claim 7, wherein development of mucositis is prevented in the patient by administration of the composition.

9. The method of claim 1, wherein the patient is a cancer patient.

10. The method of claim 1, wherein the patient has recently been, will shortly be, or is currently subject to treatment with head or neck irradiation, or stem cell or bone marrow transplantation.

11. The method of claim 1, wherein said administration step occurs prior to, concurrently with, or after a treatment that places the patient at risk of developing mucositis, or a combination thereof.

12. The method of claim 11, wherein said administration step occurs prior to a treatment that places the patient at risk of developing mucositis.

13. The method of claim 11, wherein said administration step occurs concurrently with a treatment that places the patient at risk of developing mucositis.

14. The method of claim 11, wherein said administration step occurs after treatment that places the patient at risk of developing mucositis.

15. The method of claim 11, wherein said administration step occurs concurrently with a treatment that places the patient at risk of developing mucositis, further comprising a step of administering the composition at least once during days 0-3 after the treatment that places the patient at risk of developing mucositis.

16. The method of claim 11, wherein the treatment that places the patient at risk of developing mucositis comprises radiation therapy.

17. The method of claim 11, wherein the treatment that places the patient at risk of developing mucositis comprises chemotherapy.

18. The method of claim 1, further comprising the step of administering antimicrobial therapy to the patient.

19. The method of claim 18, wherein the antimicrobial therapy is antibiotic therapy.

* * * * *